US008889738B2

(12) United States Patent
Dhal et al.

(10) Patent No.: US 8,889,738 B2
(45) Date of Patent: *Nov. 18, 2014

(54) AMIDO-AMINE POLYMER COMPOSITIONS

(75) Inventors: Pradeep K. Dhal, Westford, MA (US); Stephen Randall Holmes-Farley, Arlington, MA (US); Chad C. Huval, Somerville, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/417,592

(22) Filed: Mar. 12, 2012

(65) Prior Publication Data

US 2012/0237470 A1    Sep. 20, 2012

Related U.S. Application Data

(63) Continuation of application No. 12/448,222, filed as application No. PCT/US2007/025216 on Dec. 10, 2007, now Pat. No. 8,163,799.

(60) Provisional application No. 60/874,715, filed on Dec. 14, 2006.

(51) Int. Cl.
| *A61K 31/22* | (2006.01) |
| *A61K 31/04* | (2006.01) |
| *A61K 31/785* | (2006.01) |
| *A61K 31/23* | (2006.01) |
| *A61K 31/165* | (2006.01) |

(52) U.S. Cl.
CPC ............... *A61K 31/785* (2013.01); *A61K 31/23* (2013.01); *A61K 31/165* (2013.01)
USPC .......................................... 514/549; 514/740

(58) Field of Classification Search
CPC ............................ A61K 31/23; A61K 31/165
USPC .................................................. 514/549, 740
See application file for complete search history.

(56) References Cited

U.S. PATENT DOCUMENTS

| 3,332,841 | A | 7/1967 | Ainsworth et al. |
| 3,383,236 | A | 5/1968 | Brindamour |
| 3,431,138 | A | 3/1969 | Zingerman et al. |
| 3,539,380 | A | 11/1970 | Johnson et al. |
| 4,115,537 | A | 9/1978 | Driscoll et al. |
| 4,211,763 | A | 7/1980 | Marshall et al. |
| 4,264,573 | A | 4/1981 | Powell et al. |
| 4,302,440 | A | 11/1981 | John et al. |
| 4,341,563 | A | 7/1982 | Kurihara et al. |
| 4,507,466 | A | 3/1985 | Tomalia et al. |
| 4,539,198 | A | 9/1985 | Powell et al. |
| 4,543,370 | A | 9/1985 | Porter et al. |
| 4,605,701 | A | 8/1986 | Harada et al. |
| 4,631,305 | A | 12/1986 | Guyer et al. |
| 4,762,524 | A | 8/1988 | Chambers et al. |
| 4,849,227 | A | 7/1989 | Cho |
| 4,871,779 | A | 10/1989 | Killat et al. |
| 4,956,182 | A | 9/1990 | Bequette et al. |
| 4,983,398 | A | 1/1991 | Gaylord et al. |
| 4,983,399 | A | 1/1991 | Maish |
| 5,073,380 | A | 12/1991 | Babu et al. |
| 5,194,464 | A | 3/1993 | Itoh et al. |
| 5,262,167 | A | 11/1993 | Vegesna et al. |
| 5,373,052 | A | 12/1994 | Fukuda et al. |
| 5,374,422 | A | 12/1994 | St. Pierre et al. |
| 5,401,515 | A | 3/1995 | Woodard et al. |
| 5,414,068 | A | 5/1995 | Bliem et al. |
| 5,430,110 | A | 7/1995 | Ahlers et al. |
| 5,447,726 | A | 9/1995 | Nomura |
| 5,455,047 | A | 10/1995 | Bequette et al. |
| 5,462,730 | A | 10/1995 | McTaggart et al. |
| 5,487,888 | A | 1/1996 | Mandeville et al. |
| 5,496,545 | A | 3/1996 | Holmes-Farley et al. |
| 5,520,932 | A | 5/1996 | McCurdy et al. |
| 5,530,092 | A | 6/1996 | Meijer et al. |
| 5,561,214 | A | 10/1996 | Yeske et al. |
| 5,607,669 | A | 3/1997 | Mandeville, III et al. |
| 5,610,268 | A | 3/1997 | Meijer et al. |
| 5,618,530 | A | 4/1997 | Mandeville, III et al. |
| 5,624,963 | A | 4/1997 | Mandeville, III et al. |
| 5,654,003 | A | 8/1997 | Fuisz et al. |
| 5,667,775 | A | 9/1997 | Holmes-Farley et al. |
| 5,679,717 | A | 10/1997 | Mandeville, III et al. |
| 5,686,106 | A | 11/1997 | Kelm et al. |

(Continued)

FOREIGN PATENT DOCUMENTS

| CH | 656 535 A5 | 7/1986 |
| EP | 0997148 | 5/2000 |
| EP | 1153940 | 11/2001 |
| EP | 1682606 | 7/2006 |
| EP | 1687349 | 8/2006 |
| EP | 1742613 | 1/2007 |
| EP | 0211991 | 3/2007 |
| EP | 1831266 | 9/2007 |
| JP | 60152424 A | 8/1985 |
| JP | 10316576 A | 12/1998 |
| JP | 2000178182 A | 6/2000 |
| WO | WO 93/00915 | 1/1993 |

(Continued)

OTHER PUBLICATIONS

Jayamurugan, Govindasamy, et al., "Synthesis of Large Generation poly(propul ether imine) (PETIM) Dendrimers" *Tetrahedron*, 62 (2006) 9582-9588.

(Continued)

*Primary Examiner* — Raymond Henley, III
(74) *Attorney, Agent, or Firm* — Genzyme Corporation

(57) ABSTRACT

Compounds, polymers, crosslinked polymers and pharmaceutical compositions comprising the same may be derived from multi-amine monomers and multi-functional monomers having two or more amine reactive groups. Such compounds, polymers, crosslinked polymers and compositions may be used to treat hyperphosphatemia or to remove ions from the gastrointestinal tract of animals, including humans.

15 Claims, No Drawings

(56) References Cited

U.S. PATENT DOCUMENTS

| | | |
|---|---|---|
| 5,693,675 A | 12/1997 | Mandeville, III et al. |
| 5,702,696 A | 12/1997 | Mandeville, III et al. |
| 5,703,188 A | 12/1997 | Mandeville, III et al. |
| 5,709,880 A | 1/1998 | Del Corral et al. |
| 5,718,920 A | 2/1998 | Notenbomber |
| 5,747,067 A | 5/1998 | Auguello et al. |
| 5,750,148 A | 5/1998 | Maruyama et al. |
| 5,807,582 A | 9/1998 | Cha |
| 5,814,336 A | 9/1998 | Kelm et al. |
| 5,840,339 A | 11/1998 | Kunin |
| 5,840,766 A | 11/1998 | Mandeville, III et al. |
| 5,900,475 A | 5/1999 | Mandeville, III et al. |
| 5,919,832 A | 7/1999 | Mandeville, III et al. |
| 5,959,069 A | 9/1999 | Gluck et al. |
| 5,969,090 A | 10/1999 | Mandeville, III et al. |
| 5,985,938 A | 11/1999 | Holmes-Farley et al. |
| 6,022,533 A | 2/2000 | Goto et al. |
| 6,034,129 A | 3/2000 | Mandeville, III et al. |
| 6,037,444 A | 3/2000 | Rannard et al. |
| 6,083,495 A | 7/2000 | Holmes-Farley et al. |
| 6,083,497 A | 7/2000 | Huval et al. |
| 6,090,411 A | 7/2000 | Pillay et al. |
| 6,177,478 B1 | 1/2001 | Holmes-Farley et al. |
| 6,180,754 B1 | 1/2001 | Stutts et al. |
| 6,187,897 B1 | 2/2001 | Kawashima et al. |
| 6,190,650 B1 | 2/2001 | Matthews et al. |
| 6,203,785 B1 | 3/2001 | Holmes-Farley et al. |
| 6,248,318 B1 | 6/2001 | Huval et al. |
| 6,264,937 B1 | 7/2001 | Mandeville, III et al. |
| 6,281,252 B1 | 8/2001 | Holmes-Farley et al. |
| 6,284,275 B1 | 9/2001 | Chen |
| 6,362,266 B1 | 3/2002 | Buchholz et al. |
| 6,383,518 B1 | 5/2002 | Matsuda et al. |
| 6,423,754 B1 | 7/2002 | Holmes-Farley et al. |
| 6,509,013 B1 | 1/2003 | Holmes-Farley et al. |
| 6,534,600 B2 | 3/2003 | Dvornic et al. |
| 6,566,407 B2 | 5/2003 | Holmes-Farley et al. |
| 6,600,011 B2 | 7/2003 | McDonnell et al. |
| 6,605,270 B1 | 8/2003 | Mandeville, III et al. |
| 6,696,087 B2 | 2/2004 | Matsuda et al. |
| 6,726,905 B1 | 4/2004 | Mandeville, III et al. |
| 6,733,780 B1 | 5/2004 | Tyler et al. |
| 6,844,372 B2 | 1/2005 | Goto et al. |
| 6,858,203 B2 | 2/2005 | Holmes-Farley et al. |
| 6,908,609 B2 | 6/2005 | Simon et al. |
| 7,014,846 B2 | 3/2006 | Holmes-Farley et al. |
| 7,019,085 B2 | 3/2006 | Albright |
| 7,081,509 B2 | 7/2006 | Wagner et al. |
| 7,087,223 B2 | 8/2006 | Goto et al. |
| 7,101,960 B2 | 9/2006 | Mandeville, III et al. |
| 7,220,406 B2 | 5/2007 | Burke |
| 7,335,795 B2 | 2/2008 | Chang et al. |
| 7,342,083 B2 | 3/2008 | Chang et al. |
| 7,385,012 B2 | 6/2008 | Chang et al. |
| 7,449,605 B2 | 11/2008 | Chang et al. |
| 7,459,151 B2 | 12/2008 | Holmes-Farley et al. |
| 7,459,502 B2 | 12/2008 | Connor et al. |
| 7,589,238 B2 | 9/2009 | Connor et al. |
| 8,163,799 B2 * | 4/2012 | Dhal et al. .............. 514/549 |
| 2002/0054903 A1 | 5/2002 | Tyler et al. |
| 2002/0114774 A1 | 8/2002 | Fitzpatrick et al. |
| 2002/0122786 A1 | 9/2002 | Matsuda et al. |
| 2002/0159968 A1 | 10/2002 | Petersen et al. |
| 2002/0160050 A1 | 10/2002 | Elema et al. |
| 2002/0168333 A1 | 11/2002 | Burke |
| 2002/0182168 A1 | 12/2002 | Holmes-Farley et al. |
| 2002/0187120 A1 | 12/2002 | Holmes-Farley et al. |
| 2002/0187121 A1 | 12/2002 | Burke |
| 2003/0039627 A1 | 2/2003 | Holmes-Farley et al. |
| 2003/0049226 A1 | 3/2003 | Burke et al. |
| 2003/0086898 A1 | 5/2003 | Holmes-Farley et al. |
| 2003/0133902 A1 | 7/2003 | Holmes-Farley et al. |
| 2003/0175349 A1 | 9/2003 | Garg et al. |
| 2003/0180250 A1 | 9/2003 | Chauhan et al. |
| 2003/0199090 A1 | 10/2003 | Monahan et al. |
| 2004/0022844 A1 | 2/2004 | Hasenzahl et al. |
| 2004/0170695 A1 | 9/2004 | Elama et al. |
| 2004/0185111 A1 | 9/2004 | Rubino et al. |
| 2004/0191209 A1 | 9/2004 | Oba |
| 2004/0191212 A1 | 9/2004 | Holmes-Farley et al. |
| 2005/0084476 A1 | 4/2005 | Goto et al. |
| 2005/0096438 A1 | 5/2005 | Chang et al. |
| 2005/0123614 A1 | 6/2005 | Kim et al. |
| 2005/0131138 A1 | 6/2005 | Connor et al. |
| 2005/0131161 A1 | 6/2005 | Mandeville, III et al. |
| 2005/0147580 A1 | 7/2005 | Connor et al. |
| 2005/0165190 A1 | 7/2005 | Chang et al. |
| 2005/0208095 A1 | 9/2005 | Hunter et al. |
| 2005/0209423 A1 | 9/2005 | Chang et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2005/0239901 A1 | 10/2005 | Chang et al. |
| 2005/0260236 A1 | 11/2005 | Tyler et al. |
| 2005/0282010 A1 | 12/2005 | Xu |
| 2006/0024336 A1 | 2/2006 | Charmot et al. |
| 2006/0029663 A1 | 2/2006 | Uchida et al. |
| 2006/0034914 A1 | 2/2006 | Tyler et al. |
| 2006/0043984 A1 | 3/2006 | Miller et al. |
| 2006/0047086 A1 | 3/2006 | Albright et al. |
| 2006/0054914 A1 | 3/2006 | Hsian Yi |
| 2006/0088592 A1 | 4/2006 | Choi et al. |
| 2006/0134225 A1 | 6/2006 | Moerck et al. |
| 2006/0171916 A1 | 8/2006 | Holmes-Farley et al. |
| 2006/0177415 A1 | 8/2006 | Burke |
| 2006/0239959 A1 | 10/2006 | Holmes-Farley et al. |
| 2006/0251614 A1 | 11/2006 | Bhagat et al. |
| 2006/0258812 A1 | 11/2006 | Gopalkrishna et al. |
| 2006/0292192 A1 | 12/2006 | Hasenzahl et al. |
| 2007/0035313 A1 | 2/2007 | Wuersch et al. |
| 2007/0059277 A1 | 3/2007 | Bhagat et al. |
| 2007/0071715 A1 | 3/2007 | DeLuca et al. |
| 2007/0094779 A1 | 5/2007 | Dauphin |
| 2007/0098678 A1 | 5/2007 | Bhagat et al. |
| 2007/0110707 A1 | 5/2007 | Ravi |
| 2007/0155950 A1 | 7/2007 | Mandeville, III et al. |
| 2007/0224283 A1 | 9/2007 | Chang et al. |
| 2008/0107737 A1 | 5/2008 | Chang et al. |
| 2008/0226735 A1 | 9/2008 | Moerck et al. |
| 2008/0292697 A1 | 11/2008 | Tyler et al. |

FOREIGN PATENT DOCUMENTS

| | | |
|---|---|---|
| WO | WO 94/19379 | 9/1994 |
| WO | WO 95/05184 | 2/1995 |
| WO | WO 96/39156 | 12/1996 |
| WO | WO 98/29107 | 7/1998 |
| WO | WO 98/42355 | 10/1998 |
| WO | WO 98/44933 | 10/1998 |
| WO | WO 99/22721 | 5/1999 |
| WO | WO 99/22743 | 5/1999 |
| WO | WO 00/22008 | 4/2000 |
| WO | WO 01/28527 | 4/2001 |
| WO | WO 2004/037274 | 5/2004 |
| WO | WO 2004/099288 | 11/2004 |
| WO | WO 2005/041900 | 5/2005 |
| WO | WO 2005/041902 | 5/2005 |
| WO | WO 2005/092039 | 10/2005 |
| WO | WO 2006/043984 | 4/2006 |
| WO | WO 2006/050314 | 5/2006 |

OTHER PUBLICATIONS

Xiuru Li, et al., "Synthesis and Characterization of Hyperbranched Poly(ester amide)s from Commercially Available Dicarboxylic Acids and Multihydroxyl Primary Amines" *Macromolecules*, 39 (2006) 7889-7899.

Pérignon, Nelly et al., "Formation and Stabilization in Water of Metal Nanoparticles by a Hyperbranched Polymer Chemically Analgous to PAMAM Dendrimers" *Chem Mater.*, 16 (2004) 4856-4858.

Koç, Fikret, et al. "Highly Regioselective Synthesis pf Amino-Functionalized Dendritic PolyGlycerols by a One Pot Hydroformylation/Reductive Amination Sequence" *J. Org. Chem.*, 70 (2005) 2021-2025.

(56) References Cited

OTHER PUBLICATIONS

Gao, Chao, "Hyperbranched copolymers made from A2, B2 and BB'2 type monomers, 3a: comparison of copoly(sulfone-amine)s containing piperazine and 4,4'-trimethylenedipiperidine units" *Macromolecular Chemistry and Physics* (2001), 202(15), 3035-3042.

Gao, Chao, "Hyperbranched polymers made from A2- and BB2'-type monomers; 3. Polyaddition of N-methyl 1,3-propanediamine to divinyl sulfone" *Macromolecular Chemistry and Physics* (2001), 202(12), 2623-2629.

Gao, Chao, "Hyperbranched copolymers made from A2, B2 and BB'2 type monomers (iv). Copolymerization of divinyl sulfone with 4,4'-trimethylenedipiperidine and N-ethylethylenediamine" *Science in China, Series B: Chemistry* (2001), 44(2), 207-215.

Gao, C., "Preparation of Water Soluble hyperbranched poly(sulfone-amine)s by polyaddition of N-ethylethylenediamine to divinyl sulfone" *Polymer* (2001), 42(18), 7603-7610.

Gao, C., "Hyperbranched polymers made from A2, B2 and BB'2 type monomers, 2. Preparation of hyperbranched copoly(sulfone-amine)s by polyaddition of N-ethylethylenediamine and piperazine to divinylsulfone" *Polymer* (2001), 42(8), 3437-3443.

Gao, Chao, "Synthesis of hyperbranched polymers from commercially available A2 and BB'2 type monomers" *Chemical Communications* (Cambridge), 1 (2001) 107-108.

Gao, Chao, "Polyaddition of B2 and BB'2 Type Monomers to A2 Type Monomer. 1. Synthesis of Highly Branched Copoly(sulfon-amine)s" *Macromolecules* (2001), 34(2), 156-161.

Yan, Deyue, "Hyperbranched Polymers Made from A2 and BB'2 Type Monomers. 1. Polyaddition of 1-(2-Aminoethyl)piperazine to Divinyl Sulfone" *Macromolecules* (2000), 33(21), 7693-7699.

Hobson, Lois J., et al. "Poly(amidoamine) Hyperbranched Systems:Synthesis, Structure and Characterization" *Polymer*, 40 (1999) 1279-1297.

Rosenbaum, Holmes-Farley, Mandeville, Pitruzzello, Goldberg, "Effect of RenaGel, a non-absorbable, cross-linked, polymeric phosphate binder, on urinary phosphorus excretion in rats" *Nephrology Dialysis Transplantation*, vol. 12 (1997) 961-964.

Mourey, T. H., et al., "Unique Behavior of Dendritic Molecules: Intrinsic Viscosity of Polyether Dendrimers" *Macromolecules*, 25 (1992) 2401-2406.

Janssen, H.M. et al, "The Synthesis and Characterization of Dendritic Molecules" Eindhoven University of Technology [No date available].

Klapper, Marcus et al., "Poly(methylene amine): A Polymer with the Maximum Possible Number of Amino Groups on a Polymer Backbone" *Angew. Chem. Int. Ed.*, 42 (2003) 4687-4690 (XP002456407).

Kuga, Shigenori, "Pore Size Ditribution Analysis of Gel Substances by Size Exclusion Chromatography" *J. Chromatography*, 206 (1981) 449-461.

Kremer, Michael, et al., "Pore-Size Distributions of Cationic Polyacrylamide Hydrogels Varying in Initial Monomer Concentration and Crosslnker/Monomer Ratio" *Macromolecules*, 27 (1994) 2965-2973.

Jansen, Johan F.G.A. et al. "The Dendritic Box: Shape-Selective Liberation of Encapsulated Guests" *J. Am. Chem. Soc.*, 117 (1995) 4417-4418.

de Brabander-van den Berg, Ellen M. M. et al., "Poly(propylenimin)-Dendrimere: Synthese in größerem Maβstab durch heterogen katalysierte Hydrierungen" *Angew. Chem.* (1993) 1370-1372. [in German only].

Duncan, Ruth et al., "Dendrimer biocompatibility and toxicity" *Advanced Drug Delivery Reviews*, 57 (2005) 2215-2237.

Huval, Chad C. et al., "Syntheses of hydrophobically modified cationic hydrogels by copolymerization of alkyl substituted diallylamine monomers and their use as bile acid sequestrants" *European Polymer Journal*, 40 (2004) 693-701.

Newkome, George R. et al., "Improved Synthesis of an Ethereal Tetraamine Core for Dendrimer Construction" *J. Org. Chem.*, 67 (2002) 3957-3960.

Schatzlein, Andreas G. et al., "Preferential liver gene expression with polypropylenimine dendrimeis" *Journal of Controlled Release*, 101 (2005) 247-258.

Shao, Lu et al., "Transport properties of cross-linked polyimide membranes induced by different generations of diaminobutane (DAB) dendrimers" *Journal of Membrane Science*, 238 (2004) 153-163.

Stasko, Nathan A. et al., "Dendrimers as a Scaffold for Nitric Oxide Release" *J. Am. Chem. Soc.*, 128 (2006) 8265-8271.

Xiao, Youchang et al., "Effects of Thermal Treatments and Dendrimers Chemical Structures on the Properties of Highly Surface Cross-Linked Polyimide Films" *Ind. Eng. Chem. Res.*, 44 (2005) 3059-3067.

Bhadra, D. et al., "Glycodendrimeric Nanoparticulate Carriers of Primaquine Phosphate for Liver Targeting" *International Journal of Pharmaceutics*, 295 (Mar. 2005) 221-233.

Pavlov, G. M. et al. "Molecular Characteristics of Poly(propylene imine) Dendrimers as Studied with Translational Diffusion and Viscometry" *Colloid. Polym. Sci.*, 280 (2002) 416-423.

Chertow, Glenn M. et al. "The Effects of Sevelamer and Calcium Acetate on Proxies of Atherosclerotic and Arteriosclerotic Vascular Disease in Hemodialysis Patients" *Am. J. Nephrol.*, 23:5 (2003) 307-314.

Katopodis, K. P. et al. "Effectiveness of Aluminum Hydroxide Timing Administration in Relation to Meals in Controlling Hyperphosphatemia in Dialysis Patients" *The International Journal of Artificial Organs*, 28:8 (2005) 803-807.

Selmeczi, B. et al. "Investigations of the Influence of Some Novel Auxiliary Agents on the Physical Properties of Tablets" *Pharmaceutical Technological Institute of the Medical University of Szeged* (Hungary), [No date available].

Mattsson, S. et al. "Formulation of High Tensile Strength Rapidly Disintegrating Tablets Evaluation of the Effect of Some Binder Properties" *S.T.P. Pharma Sciences*, 11:3 (2001) 211-220.

Soltero, Richard et al. "The Effects of PH. Ionic Concentration and Ionic Species of Dissolution Media on the Release Rates of Quinidine Gluconate Sustained Release Dosage Forms" *Drug Development and Industrial Pharmacy*, 17:1 (1991) 113-140.

Hammouda, Y. et al. "The Use of Sodium Chloride as a Directly Compressible Filler in Therapeutic Tablets" *Pharm. Ind.*, 37:5 (1975) 361-363.

Caramella, Carla et al. "Experimental Evidence of Disintegration Mechanisms" *Acta Pharm. Technol.*, 35:1 (1989) 30-33.

Tirkkonen, Sirpa et al. "Enhancement of Drug Release from Ethylcellulose Microcapsules Using Solid Sodium Chloride in the Wall" *International Journal of Pharmaceutics*, 88 (1992) 39-51.

Mitchell, Karen et al. "The Influence of Additives on the Cloud Point, Disintegration and Dissolution of Hydroxypropylmethylcellulose Gels and Matrix Tablets" *International Journal of Pharmaceutics*, 66 (1990) 233-242.

Tirkkonen, Sirpa et al. "Release of Indomethacin from Tabletted Ethylcellulose Microcapsules" *International Journal of Pharmaceutics*, 92 (1993) 55-62.

Ferrari, F. et al. "Investigation on Bonding and Distintegration Properties of Pharmaceutical Materials" *International Journal of Pharmaceutics*, 136 (1996) 71-79.

Lin, Shan-Yang et al. "Influence of Excipients, Drugs, and Osmotic Agent in the Inner Core on the Time-Controlled Disintegration of Compression-Coated Ethylcellulose Tablets" *Journal of Pharmaceutical Sciences*, 91:9 (Sep. 2002) 2040-2046.

Schulz, W. "Brief Evaluation: Sevelamer Hydrochloride" *Drug, Therapy Criticism*, Hans Marseille Publishers GmbH, Munich, Issue 3 (2001) 621-626.

Maroni, Bradley J. et al. "Renal Bioreplacement Therapy is Associated with a Reduction in Mortality in Patients with Acute Renal Failure: Results of a Randomized, Multi-Center, Phase II Trial" ERA-EDTA: Abstract #551794 (2006).

"Renvela: sevelamer carbonate" Prescribing Information, Genzyme Corporation, Nov. 2007.

International Search Report dated Apr. 4, 2008 for PCT/US2007/025216.

* cited by examiner

AMIDO-AMINE POLYMER COMPOSITIONS

CROSS-REFERENCE TO RELATED APPLICATIONS

This application is a continuation of U.S. patent application Ser. No. 12/448,222, filed Dec. 8, 2009, now U.S. Pat. No. 8,163,799, which is the National Phase application of International Application No. PCT/US2007/025216, filed Dec. 10, 2007, which designates the United States and was published in English, and which further claims the benefit of priority from U.S. Provisional Application No. 60/874,715, filed Dec. 14, 2006. These applications, in their entirety, are incorporated herein by reference.

FIELD OF THE INVENTION

This invention relates to polymers, copolymers, polymer networks and/or copolymer networks for binding target ions, and more specifically relates to pharmaceutically acceptable compositions, polymers, copolymers, polymer networks and/or copolymer networks for binding target ions.

BACKGROUND OF THE INVENTION

Hyperphosphatemia frequently accompanies diseases associated with inadequate renal function such as end stage renal disease (ESRD), hyperparathyroidism, and certain other medical conditions. The condition, especially if present over extended periods of time, leads to severe abnormalities in calcium and phosphorus metabolism and can be manifested by aberrant calcification in joints, lungs, and eyes.

Therapeutic efforts to reduce serum phosphate include dialysis, reduction in dietary phosphate, and oral administration of insoluble phosphate binders to reduce gastrointestinal absorption. Many such treatments have a variety of unwanted side effects and/or have less than optimal phosphate binding properties, including potency and efficacy. Accordingly, there is a need for compositions and treatments with good phosphate-binding properties and good side effect profiles.

BRIEF SUMMARY OF THE INVENTION

The present invention relates to polymers, copolymers, polymer networks, copolymer networks and/or pharmaceutical compositions comprising the same. The polymers and copolymers can be crosslinked to form polymer networks and copolymer networks respectively. Compositions can comprise polymers or residues thereof, copolymers or residues thereof, polymer networks and/or copolymer networks. Several embodiments of the invention are described in further detail as follows. Generally, each of these embodiments can be used in various and specific combinations, and with other aspects and embodiments unless otherwise stated herein.

In addition to the polymers, copolymers, polymer networks and copolymer networks of the present invention as described herein, other forms of the polymers, copolymers, polymer networks and copolymer networks are within the scope of the invention including pharmaceutically acceptable salts, solvates, hydrates, prodrugs, polymorphs, clathrates, and isotopic variants and mixtures thereof of polymers, copolymers, polymer networks and/or copolymer networks described herein.

In addition, polymers, copolymers, polymer networks, and copolymer networks of the invention may have optical centers, chiral centers or double bonds and the polymers, copolymers, polymer networks and copolymer networks of the present invention include all of the isomeric forms of these polymers, copolymers, polymer networks and copolymer networks, including optically pure forms, racemates, diastereomers, enantiomers, tautomers and/or mixtures thereof.

The invention provides methods of treating an animal, including a human. The method generally involves administering an effective amount of a polymer, copolymer, polymer network and/or a copolymer network or a composition (e.g., a pharmaceutical composition) comprising the same as described herein.

In some embodiments, the invention is, consists essentially of, or comprises a copolymer or residue thereof and/or a copolymer network or a pharmaceutical composition comprising the same, where the copolymer is derived from two or more monomers or comprises a residue of two or more monomers where the monomers comprise a multi-amine monomer and a multifunctional monomer comprising two or more amine-reactive groups.

In one embodiment, the invention is, consists essentially of, or comprises a copolymer or residue thereof and/or a copolymer network that is derived from at least one monomer represented by Formula I and at least one monomer represented by Formula II as follows:

wherein $R_1$ independently represents a hydrogen radical, $-RNH_2$, $-R-N-(R-NH_2)_2$ or $-R-N-(R-N-(R-NH_2)_2)_2$, wherein R independently represents a branched or unbranched, substituted or unsubstituted alkyl radical, for example a $C_1$ to $C_{20}$ radical such as a $C_1$, $C_2$, $C_3$, $C_4$, $C_5$, or $C_6$ radical, with the proviso that at least one $R_1$, such as one, two or three $R_1$'s, is not a hydrogen radical; $R_2$ independently represents a hydrogen radical or a branched or unbranched, substituted or unsubstituted alkyl radical, for example a $C_1$ to $C_{20}$ radical such as a $C_1$, $C_2$, $C_3$, $C_4$, $C_5$, or $C_6$ radical.

Another aspect of the invention is a pharmaceutical composition comprising one or more polymers, copolymers, polymer networks and/or copolymer networks of the present invention and at least one pharmaceutically acceptable excipient. The polymers, copolymers, polymer networks and/or copolymer networks described herein have several therapeutic applications. For example, they are useful in removing compounds or ions such as anions, for example phosphorous-containing compounds or phosphorous containing ions such as organophosphates and/or phosphates, from the gastrointestinal tract, such as from the stomach, small intestine and/or large intestine. In some embodiments, the polymers, copolymers, polymer networks and/or copolymer networks are used in the treatment of phosphate imbalance disorders and renal diseases.

In some embodiments, the invention comprises polymers and/or copolymers formed using a one pot or single step synthesis and polymer networks, copolymer networks and/or pharmaceutical compositions formed therefrom.

In yet another aspect, the polymers, copolymers, polymer networks and/or copolymer networks are useful for removing other solutes, such as chloride, bicarbonate, and/or oxalate containing compounds or ions. Polymers, copolymers, polymer networks and/or copolymer networks removing oxalate compounds or ions find use in the treatment of oxalate imbalance disorders. Polymers, copolymers, polymer networks and/or copolymer networks removing chloride compounds or ions find use in, for example, treating acidosis. In some embodiments, the polymers, copolymers, polymer networks and/or copolymer networks are useful for removing bile acids and related compounds.

The invention further provides compositions containing any of the polymers, copolymers, polymer networks and/or copolymer networks described herein where the polymers, copolymers, polymer networks and/or copolymer networks are in the form of particles and where the particles are encased in one or more shells.

In another aspect, the invention provides pharmaceutical compositions. In one embodiment, the pharmaceutical composition contains one or more polymers, copolymers, polymer networks and/or copolymer networks of the invention and a pharmaceutically acceptable excipient. In some embodiments, the composition is a liquid formulation in which the polymer, copolymer, polymer network and/or copolymer network is dispersed in a liquid vehicle, such as water, and suitable excipients. In some embodiments, the invention provides a pharmaceutical composition comprising a polymer, copolymer, polymer network and/or copolymer network for binding a target compound or ion, and one or more suitable pharmaceutical excipients, where the composition is in the form of a tablet, sachet, slurry, food formulation, troche, capsule, elixir, suspension, syrup, wafer, chewing gum or lozenge. In some embodiments the composition contains a pharmaceutical excipient selected from the group consisting of sucrose, mannitol, xylitol, maltodextrin, fructose, sorbitol, and combinations thereof. In some embodiments the target anion of the polymer, copolymer, polymer network and/or copolymer network is an organophosphate and/or phosphate. In some embodiments the polymer, copolymer, polymer network and/or copolymer network is more than about 50% of the weight of the tablet. In some embodiments, the tablet is of cylindrical shape with a diameter of from about 12 mm to about 28 mm and a height of from about 1 mm to about 8 mm and the amine polymer comprises more than 0.6 to about 2.0 gm of the total weight of the tablet.

In some of the compositions of the invention, the excipients are chosen from the group consisting of sweetening agents, binders, lubricants, and disintegrants. Optionally, the polymer, copolymer, polymer network and/or copolymer network is present as particles of less than about 80 μm mean diameter. In some of these embodiments, the sweetening agent is selected from the group consisting of sucrose, mannitol, xylitol, maltodextrin, fructose, and sorbitol, and combinations thereof.

In some embodiments, the invention provides copolymers, copolymer networks, or compositions that comprise a copolymer or residue thereof, where the copolymer is derived from two or more comonomers comprising at least one multi-amine or residue thereof and at least one multi-ester or residue thereof.

In some embodiments, the invention comprises a polymer, copolymer, polymer network or copolymer network, where the polymer or copolymer is formed from the alkylation of one or more multi-amine compounds with one or more substituted or unsubstituted α,β-unsaturated carboxylic acids to form at least one multi-amine ester, followed by reaction (e.g., polycondensation) of the multi-amine ester.

In some embodiments, polymers and/or copolymers of the invention may comprise hyperbranched polymers. In some embodiments, polymers and/or copolymers of the invention include polymers and/or copolymers where from 10-95% of the amine groups in the polymer and/or copolymer comprise secondary amine groups. In other embodiments, polymers and/or copolymers of the invention may have a degree of branching of from 0.10 to 0.95. In other embodiments, polymers and/or copolymers of the invention have a polydispersity of greater than 1.2. In some embodiments, polymers and/or copolymers of the invention may be branched and may be characterized by a plot of log ($M_v$) versus log ($\eta$) that has no maximum, where $M_v$ represents the viscosity averaged molecular weight of the polymer and $\eta$ represents the intrinsic viscosity of the polymer. In other embodiments, polymers and/or copolymers of the invention include polymers and or copolymers where greater than 10% and less than 90% of the non-terminal, non-amido amine groups in the polymer or copolymer are tertiary amines. In some embodiments, the invention comprises polymer networks or copolymer networks formed from polymers or copolymers having any one or more of these properties, methods of treatment, for example treatment of hyperphosphatemia comprising administering an effective amount of one or more polymers, copolymers, polymer networks, copolymer networks or compositions (e.g., pharmaceutical compositions) comprising the same to an animal in need thereof, where the polymers or copolymers have any one or more of these properties.

In still other embodiments, a polymer network and/or copolymer network may include two or more polymers or copolymers, where at least one of the polymers or copolymers is a derived from monomers according to Formulas I and II, that may be linked or crosslinked to form a polymer network or copolymer network. For example, in some embodiments a polymer network or copolymer network may comprise a residue of two or more polymers or copolymers according to the invention and a residue of one or more crosslinking agents.

DETAILED DESCRIPTION OF THE INVENTION

In one aspect, the invention is, consists essentially of, or comprises a hyperbranched polymer or residue thereof, a hyperbranched copolymer or residue thereof, a hyperbranched polymer network and/or a hyperbranched copolymer network or a pharmaceutical composition comprising the same.

In another aspect, the present invention provides copolymers, copolymer networks that comprise said copolymers or residues thereof, compositions (e.g., pharmaceutical compositions) that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymer is derived from or comprises a residue of a multi-amine monomer and a residue of a multifunctional monomer comprising two or more amine-reactive groups such as, for example, vinyl groups, carboxylic acid groups, ester groups and/or combinations thereof. The amine-reactive groups may react with the multi-amine via any suitable reaction, for example via a condensation or polycondensation reaction or via an alkylation reaction. In some embodiments, the reaction may include a combination of different reactions, such as a combination of alkylation and condensation reactions. In some embodiments the reaction or reactions may be controlled by any suitable means including, for example, choice of solvent, temperature, concentration of reactants, protection using protecting groups, pH and/or any other suitable methods.

In some embodiments, the present invention provides polymers and/or polymer networks that comprise polymers or residues thereof, compositions (e.g., pharmaceutical compositions) that comprise polymers, and/or polymer networks, and methods for removing a compound or ion, such as a phosphorous-containing compound or a phosphorous-containing ion (e.g. phosphate) from the gastrointestinal tract of an animal by administering an effective amount of a polymer or polymer network, where the polymers are derived from a monomer or comprise a residue of a monomer, where the monomer comprises an amine ester monomer having one or more amine reactive groups and one or more amine groups.

In one aspect, the present invention provides copolymers, copolymer networks that comprise said copolymers or residues thereof, compositions (e.g., pharmaceutical compositions) that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymers are derived from comonomers represented by the following Formulas I and II:

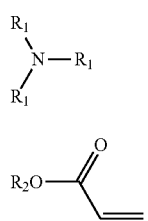

Formula I

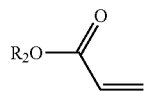

Formula II wherein $R_1$ independently represents a hydrogen radical, —$RNH_2$, —R—N—(R—$NH_2$)$_2$ or —R—N—(R—N—(R—$NH_2$)$_2$)$_2$, wherein R independently represents a branched or unbranched, substituted or unsubstituted alkyl radical for example a $C_1$ to $C_{20}$ alkyl radical, such as a $C_1$, $C_2$, $C_3$, $C_4$, $C_5$ or $C_6$ radical, with the proviso that at least one $R_1$ is not a hydrogen radical; $R_2$ independently represents a hydrogen radical or a branched or unbranched, substituted or unsubstituted alkyl radical for example a $C_1$ to $C_{20}$ alkyl radical, such as a $C_1$, $C_2$, $C_3$, $C_4$, $C_5$ or $C_6$ radical.

In some embodiments, the present invention provides copolymers, copolymer networks that comprise said copolymers or residues thereof, compositions (e.g., pharmaceutical compositions) that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymers comprise at least one multi-amine or residue thereof and at least one ester or multi-ester or residue thereof.

In some embodiments, the present invention provides polymers, copolymers, polymer networks that comprise polymers or residues thereof, copolymer networks that comprise copolymers or residues thereof, compositions (e.g., pharmaceutical compositions) that comprise polymers, copolymers, polymer networks and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the polymers or copolymers are formed from alkylation of multi-amine compounds with substituted or unsubstituted α,β-unsaturated carboxylic acids or esters to form at least one multi-amine ester, followed by, polycondensation of the multi-amine ester.

In another aspect, the present invention provides copolymers, copolymer networks that comprise said copolymers or residues thereof, compositions (e.g., pharmaceutical compositions) that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymers comprise a residue of one or more multi-amine compounds and a residue of one or more α,β-unsaturated carboxylic acids or esters.

In some embodiments, the present invention provides polymers and/or polymer networks that comprise polymers or residues thereof, compositions (e.g., pharmaceutical compositions) that comprise polymers, and/or polymer networks, and methods for removing a compound or ion, such as a phosphorous-containing compound or a phosphorous-containing ion (e.g. phosphate) from the gastrointestinal tract of an animal by administering an effective amount of a polymer or polymer network, where the polymers comprise polycondensation polymers derived from one or more multi-amine ester monomers.

In some embodiments, the present invention provides polymers, polymer networks that comprise said polymers or residues thereof, compositions (e.g., pharmaceutical compositions) that comprise polymers and/or polymer networks, and methods for removing a compound or ion, such as a phosphorous-containing compound or a phosphorous-containing ion (e.g. phosphate) from the gastrointestinal tract of an animal by administering an effective amount of a polymer or polymer network, where the polymer is derived from a vinyl amide monomer, said monomer comprising one or more vinyl groups and one or more non-amido amine groups.

In some embodiments, polymers and/or copolymers of the invention include polymers and or copolymers where from 10-95%, for example 10-75%, 25%-75%, 30%-60%, such as 20%, 25%, 30%, 35%, 40%, 45%, 50%, or 55% of the amine groups in the polymer or copolymer comprise secondary amine groups. In other embodiments, polymers and/or copolymers of the invention include polymers and or copolymers where greater than 10% and less than 90%, for example, from 15%-85%, 20%-80%, 30%-70%, such as 35%, 40%, 45%, 50%, 55%, 60% or 65% of the non-terminal, non-amido amine groups in the polymer or copolymer are tertiary amines. In other embodiments, polymers and/or copolymers of the invention may have a degree of branching of from 0.10 to 0.95, such as from 0.25-0.75, 0.30-0.60, or such as a degree of branching of 0.2, 0.25, 0.3, 0.35, 0.4, 0.45, 0.5, 0.55 which, in some embodiments may be calculated according to the following formula:

$$\text{Degree of Branching} = \frac{N_p + N_t}{N_p + N_t + N_s}$$

where
$N_p$=the number of primary amine units in the polymer (e.g.,

units);
$N_t$=the number of tertiary amine units in the polymer (e.g.,

units; and
$N_s$=the number of secondary amine units in the polymer (e.g.,

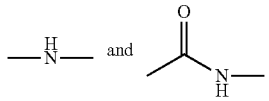

units).

In other embodiments, polymers and/or copolymers of the invention have a polydispersity of greater than 1.2, for example greater than 1.3, 1.4, 1.5, 1.75, 2.0, 2.5 or even greater than 3.0, such as from 1.2-6, such as 1.5-5 or 2-4. In some embodiments, polymers and/or copolymers of the invention may be branched and may be characterized by a plot of log ($M_v$) versus log ($\eta$) that has no maximum, where $M_v$ represents the viscosity averaged molecular weight of the polymer or copolymer and $\eta$ represents the intrinsic viscosity of the polymer or copolymer. For example, in some embodiments, polymers and copolymers of the invention where the following equation is true: $d(\log(\eta))/d(\log(M_v)) \neq 0$.

In some embodiments, polymers and/or copolymers of the invention may have random, variable length branching. For example, polymers or copolymers of the invention may exhibit branching that does not conform to a regular or easily predictable or quantifiable pattern of occurrence or length and instead results from essentially random molecular interactions that may be driven by a wide variety of different variables such as, for example, monomer concentration, reactivity, pH, solvent, temperature, charge-charge interactions, catalysis, order of addition, and any other reaction parameters.

As used herein, unless otherwise stated, the term "derived from" is understood to mean: produced or obtained from another substance by chemical reaction, especially directly derived from the reactants, for example a polymer or copolymer may be derived from the reaction of a multi-amine compound and a substituted or un-substituted α,β unsaturated carboxylic acid or ester. Additionally, a polymer or copolymer that is reacted with a linking agent, such as a crosslinking agent results in a polymer network or a copolymer network that is derived from the polymer or copolymer and the linking agent.

In some embodiments, the present invention provides copolymers, copolymer networks that comprise said copolymers or residues thereof, compositions (e.g., pharmaceutical compositions) that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymers are derived from comonomers represented by the following Formulas I and II:

Formula I

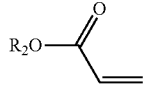

Formula II wherein $R_1$ independently represents a hydrogen radical, —$RNH_2$, —R—N—(R—$NH_2$)$_2$ or —R—N—(R—N—(R—$NH_2$)$_2$)$_2$, wherein R independently represents a branched or unbranched, substituted or unsubstituted alkyl radical for example a $C_1$ to $C_{20}$ alkyl radical, such as a $C_1$, $C_2$, $C_3$, $C_4$, $C_5$ or $C_6$ radical, with the proviso that at least one $R_1$ is not a hydrogen radical; $R_2$ independently represents a hydrogen radical or a branched or unbranched, substituted or unsubstituted alkyl radical for example a $C_1$ to $C_{20}$ alkyl radical, such as a $C_1$, $C_2$, $C_3$, $C_4$, $C_5$ or $C_6$ radical where the copolymer is hyperbranched.

In some embodiments, the present invention provides copolymers, copolymer networks that comprise said copolymers or residues thereof, compositions (e.g., pharmaceutical compositions) that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymers comprise a compound or residue thereof according to the following Formula I and a compound or residue thereof according to the following Formula II

Formula I

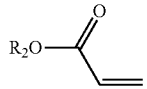

Formula II wherein $R_1$ independently represents a hydrogen radical, —$RNH_2$, —R—N—(R—$NH_2$)$_2$ or —R—N—(R—N—(R—$NH_2$)$_2$)$_2$, wherein R independently represents a branched or unbranched, substituted or unsubstituted alkyl radical for example a $C_1$ to $C_{20}$ alkyl radical, such as a $C_1$, $C_2$, $C_3$, $C_4$, $C_5$ or $C_6$ radical, with the proviso that at least one $R_1$ is not a hydrogen radical; $R_2$ independently represents a hydrogen radical or a branched or unbranched, substituted or unsubstituted alkyl radical for example a $C_1$ to $C_{20}$ alkyl radical, such as a $C_1$, $C_2$, $C_3$, $C_4$, $C_5$ or $C_6$ radical where the copolymer has one or more of the following characteristics:
  a degree of branching of from 0.10 to 0.95;
  from 10-95% of the nitrogen atoms in the copolymer are the nitrogen in a secondary amine moiety;
  a polydispersity greater than about 1.2;
  random, variable length branching;
  greater than 10% and less than 90% of non-terminal, non-amido amine groups in said copolymer comprise tertiary amines;

when branched, an intrinsic viscosity that has no maximum (versus viscosity averaged molecular weight).

In some embodiments, the compound or comonomer according to Formula I is selected from the group consisting of:

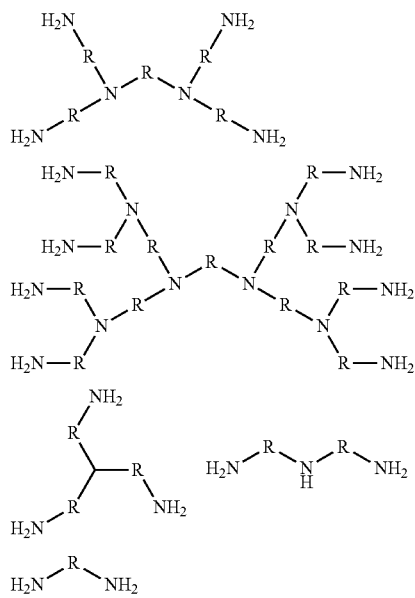

and combinations thereof, where R independently represents a branched or unbranched, substituted or unsubstituted alkyl radical for example a $C_1$ to $C_{20}$ alkyl radical, such as a $C_1$, $C_2$, $C_3$, $C_4$, $C_5$ or $C_6$ radical. Examples of compounds or comonomers according to Formula I include:

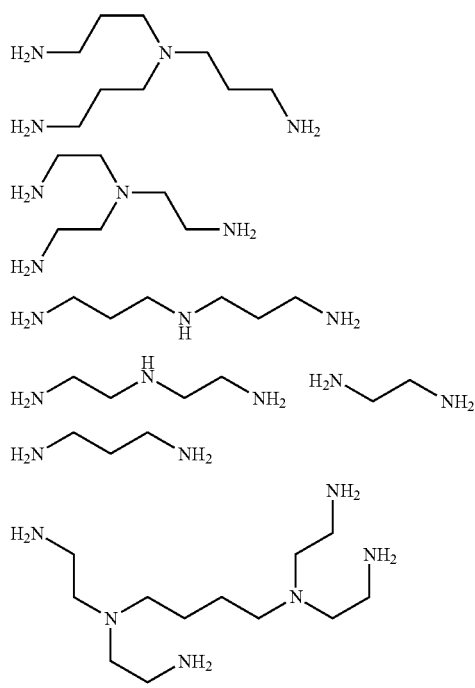

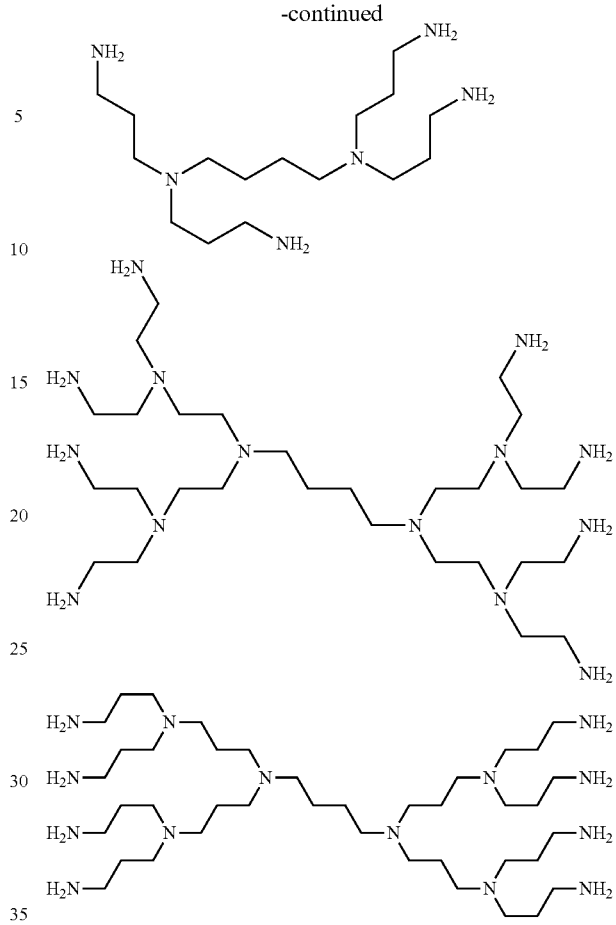

In some embodiments, the compound or comonomer according to Formula II is selected from the group consisting of:

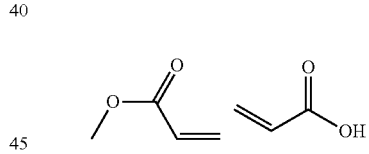

and combinations thereof.

In some embodiments, the present invention provides copolymers, copolymer networks that comprise said copolymers or residues thereof, compositions (e.g., pharmaceutical compositions) that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymers comprise at least one multi-amine or residue thereof and at least one ester or multi-ester or residue thereof; where the copolymer has one or more of the following characteristics:
- a degree of branching of from 0.10 to 0.95;
- from 10-95% of the nitrogen atoms in the copolymer are the nitrogen in a secondary amine moiety;
- a polydispersity greater than about 1.2;
- random, variable length branching;
- greater than 10% and less than 90% of non-terminal, non-amido amine groups in said copolymer comprise tertiary amines;

when branched, an intrinsic viscosity that has no maximum (versus viscosity averaged molecular weight).

In some embodiments, the multi-amine comprises a compound according to Formula I. In some embodiments the multi-amine may have from 2-20, such as 3, 4, 5, 6, 7, 8, 9, 10, 11, 12, 13, 14, 15, 16, 17, 18 or 19 terminal amine groups and the multi-ester may have from 2-20, such as 3, 4, 5, 6, 7, 8, 9, 10, 11, 12, 13, 14, 15, 16, 17, 18 or 19 terminal ester groups. In some embodiments the multi-ester is selected from the group consisting of:

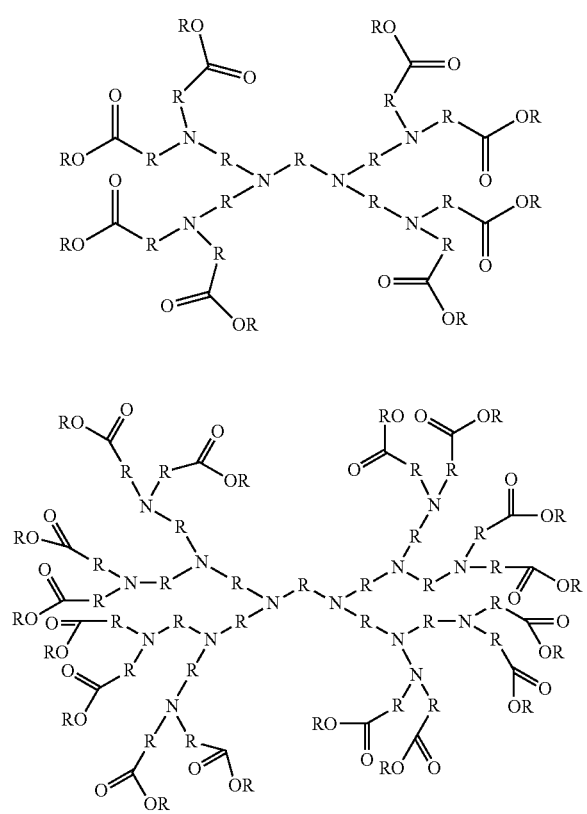

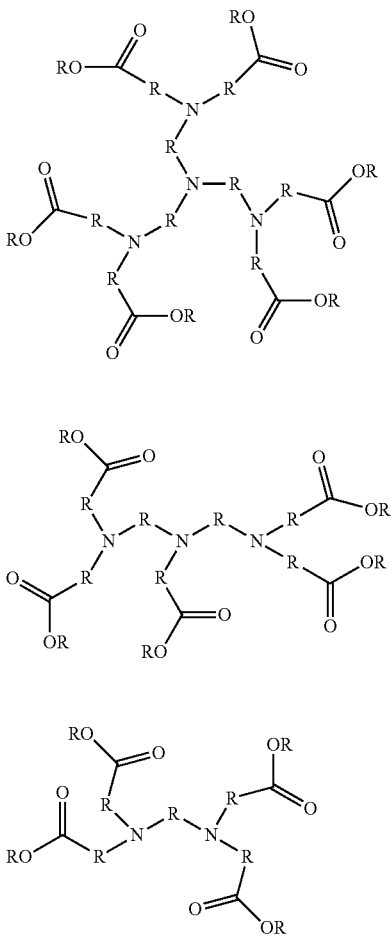

and combinations thereof, where R independently represents a branched or unbranched, substituted or unsubstituted alkyl radical for example a $C_1$ to $C_{20}$ alkyl radical, such as a $C_1$, $C_2$, $C_3$, $C_4$, $C_5$ or $C_6$ radical.

Examples of some multi-esters include:

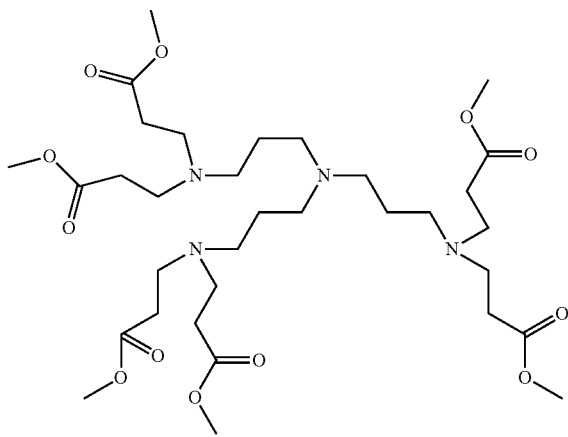

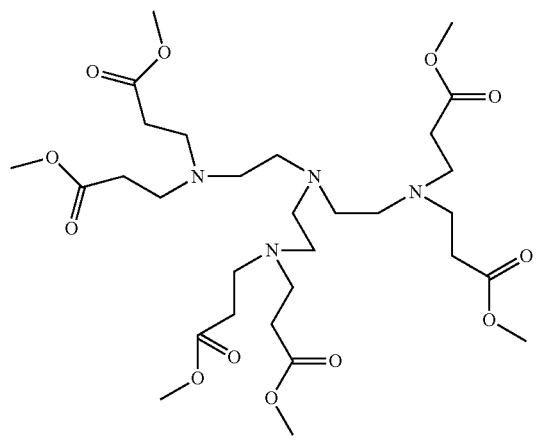

-continued
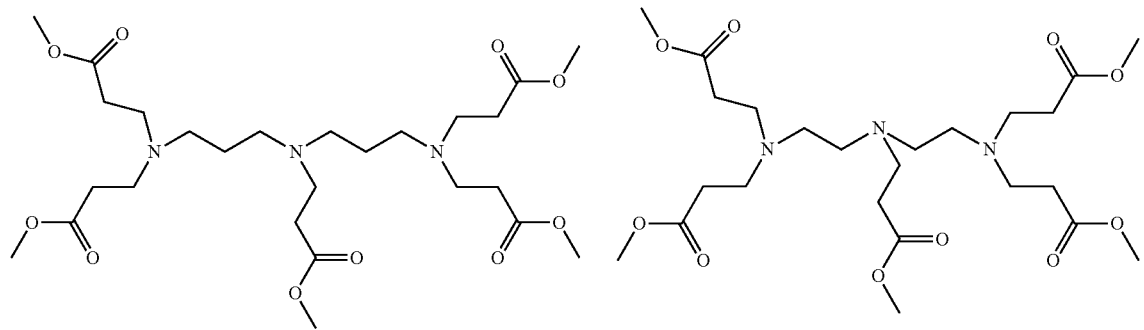
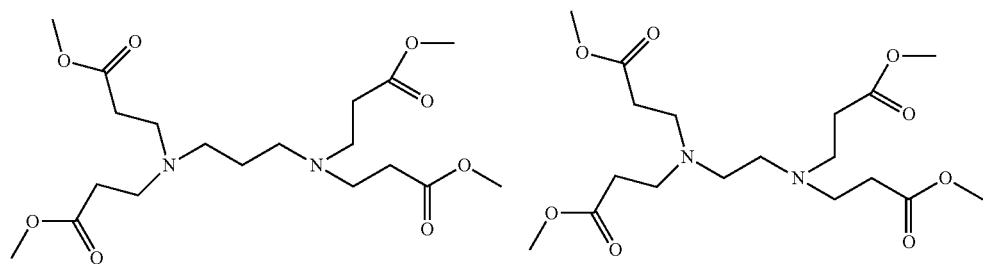
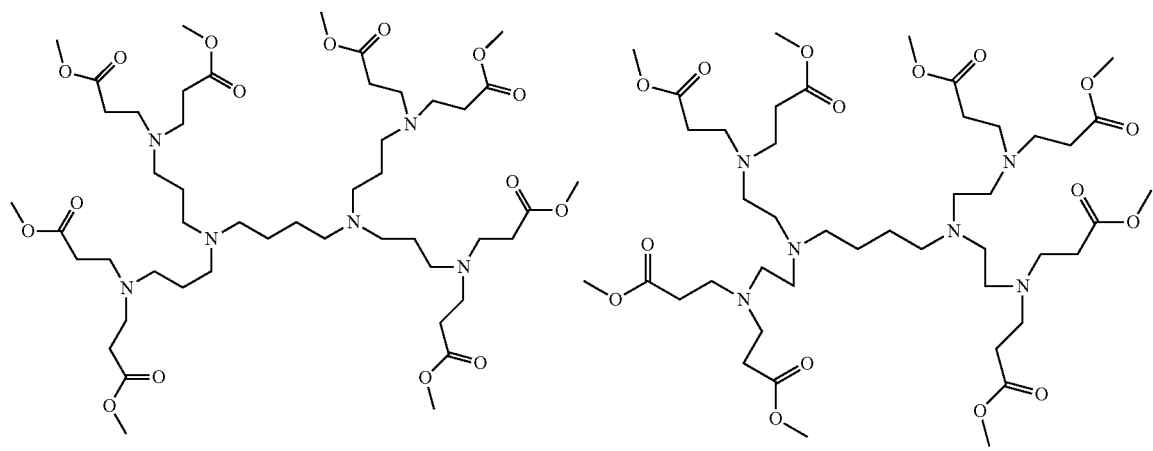

-continued
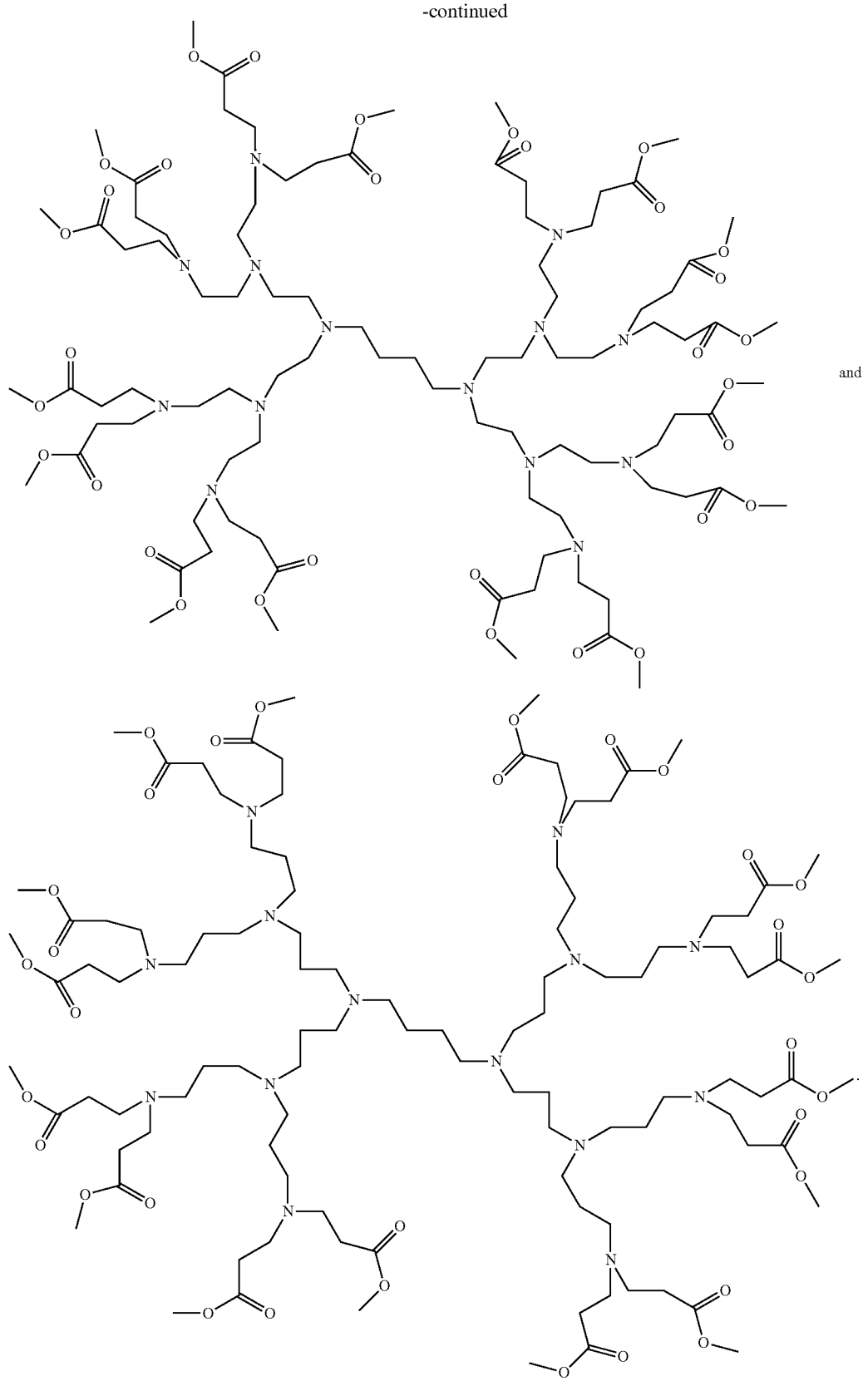
and
In some embodiments, the present invention provides polymers, copolymers, polymer networks that comprise polymers or residues thereof, copolymer networks that comprise copolymers or residues thereof, compositions (e.g., pharmaceutical compositions) that comprise polymers, copolymers, polymer networks and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the polymers or copolymers are formed from alkylation of multi-amine compounds, such as, for example multi-amine compounds according to Formula I, with substituted or unsubstituted α,β-unsaturated carboxylic acids or esters to form at least one multi-amine ester, followed by, polycondensation of the multi-amine ester where the polymer or copolymer has one or more of the following characteristics:

a degree of branching of from 0.10 to 0.95;
from 10-95% of the nitrogen atoms in the copolymer are the nitrogen in a secondary amine moiety;
a polydispersity greater than about 1.2;
random, variable length branching;
greater than 10% and less than 90% of non-terminal, non-amido amine groups in said copolymer comprise tertiary amines;
when branched, an intrinsic viscosity that has no maximum (versus viscosity averaged molecular weight).

In some embodiments, polycondensation comprises polymerization of the at least one multi-amine ester. In other embodiments, polycondensation comprises copolymerization of the at least one multi-amine ester with one or more multi-amine compounds that may be the same or different than the multi-amine compound that forms the multi-amine ester.

In some embodiments, the present invention provides polymers and/or polymer networks that comprise polymers or residues thereof, compositions (e.g., pharmaceutical compositions) that comprise polymers, and/or polymer networks, and methods for removing a compound or ion, such as a phosphorous-containing compound or a phosphorous-containing ion (e.g. phosphate) from the gastrointestinal tract of an animal by administering an effective amount of a polymer or polymer network, where the polymers comprise polycondensation polymers derived from one or more multi-amine ester monomers where the polycondensation polymers have one or more of the following characteristics:

a degree of branching of from 0.10 to 0.95;
from 10-95% of the nitrogen atoms in the polymer are the nitrogen in a secondary amine moiety;
a polydispersity greater than about 1.2;
random, variable length branching;
greater than 10% and less than 90% of non-terminal, non-amido amine groups in said polymer comprise tertiary amines;
when branched, an intrinsic viscosity that has no maximum (versus viscosity averaged molecular weight).

In some embodiments the multi-amine ester monomer may be selected from the group consisting of

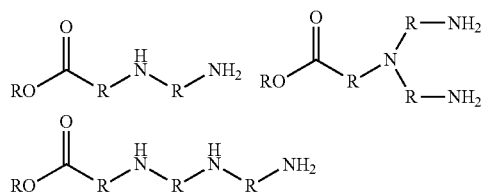

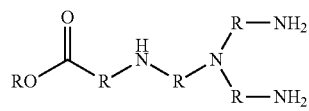

and combinations thereof.

In some embodiments, the present invention provides copolymers, copolymer networks that comprise said copolymers or residues thereof, compositions that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymers comprise at least one compound or residue thereof, said compound represented by the following Formula III:

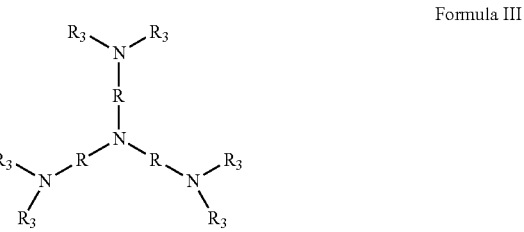

Formula III wherein R independently represents a branched or unbranched, substituted or unsubstituted alkyl radical for example a $C_1$ to $C_{20}$ alkyl radical, such as a $C_1$, $C_2$, $C_3$, $C_4$, $C_5$ or $C_6$ radical; $R_3$ independently represents a hydrogen radical or a unit independently represented by the following Formula IV, with the proviso that at least one $R_3$ comprises a group represented by Formula IV:

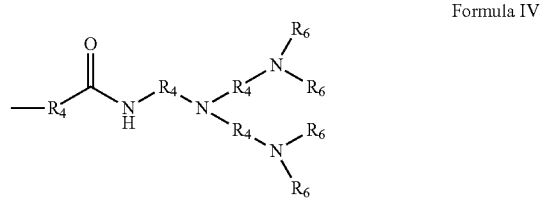

Formula IV wherein $R_4$ independently represents

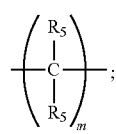

wherein m independently represents an integer from 1-20; $R_5$ independently represents a hydrogen radical; a substituted or un-substituted alkyl radical; a substituted or un-substituted aryl radical; or $R_5$ and a neighboring $R_5$ together represent a link or links comprising a residue of a crosslinking agent, a substituted or un-substituted alicyclic radical, a substituted or un-substituted aromatic radical, or a substituted or un-substituted heterocyclic radical; or $R_5$ represents a link with another compound; $R_6$ represents a hydrogen radical or a unit according to Formula IV where the copolymer has one or more of the following characteristics:
  a degree of branching of from 0.10 to 0.95;
  from 10-95% of the nitrogen atoms in the copolymer are the nitrogen in a secondary amine moiety;
  a polydispersity greater than about 1.2;
  random, variable length branching;
  greater than 10% and less than 90% of non-terminal, non-amido amine groups in said copolymer comprise tertiary amines;
  when branched, an intrinsic viscosity that has no maximum (versus viscosity averaged molecular weight).

In some embodiments, the copolymer comprises a residue of at least one compound, said compound represented by:

mers or residues thereof, compositions that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymers comprise at least one residue of one or more tris(aminoalkane)amines and at least one residue of a substituted or unsubstituted α,β-unsaturated carboxylic acid or ester, where the copolymer has one or more of the following characteristics:
  a degree of branching of from 0.10 to 0.95;
  from 10-95% of the nitrogen atoms in the copolymer are the nitrogen in a secondary amine moiety;
  a polydispersity greater than about 1.2;
  random, variable length branching;
  greater than 10% and less than 90% of non-terminal, non-amido amine groups in said copolymer comprise tertiary amines;
  when branched, an intrinsic viscosity that has no maximum (versus viscosity averaged molecular weight).

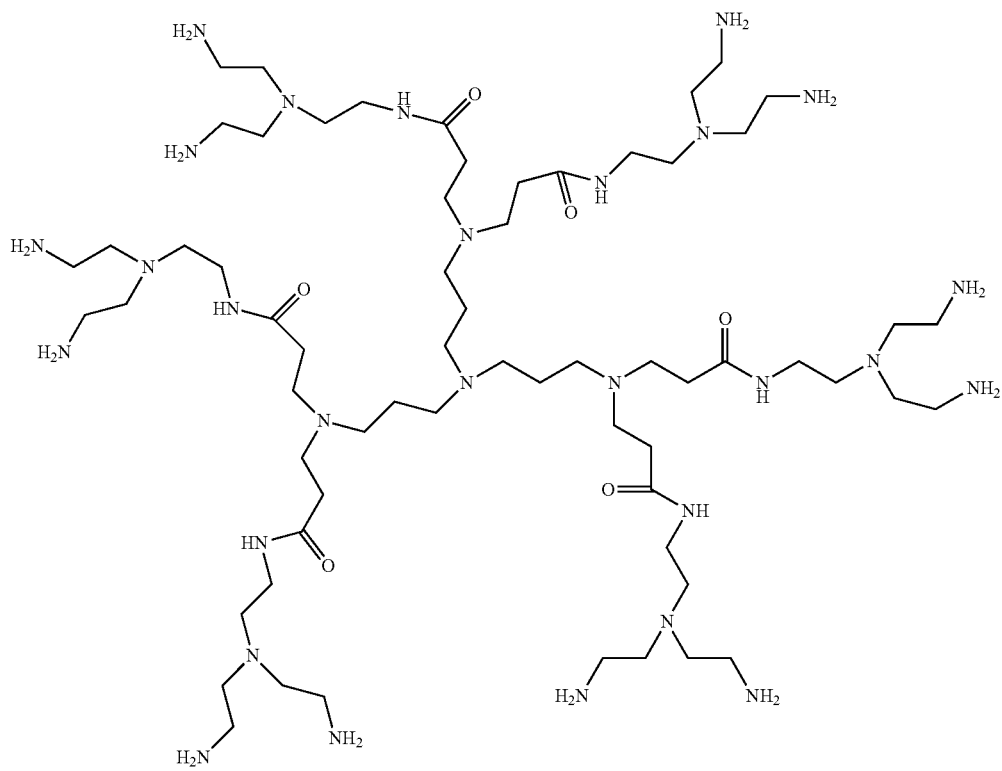 [SMILES: NCCN(CCN)CCNC(=O)CCN(CCCN(CCCN(CCC(=O)NCCN(CCN)CCN)CCC(=O)NCCN(CCN)CCN)CCCN(CCC(=O)NCCN(CCN)CCN)CCC(=O)NCCN(CCN)CCN)CCC(=O)NCCN(CCN)CCN]

In some embodiments, the present invention provides copolymers, copolymer networks that comprise said copoly- In some embodiments the copolymer comprises one or more groups represented by the following Formula V:

Formula V

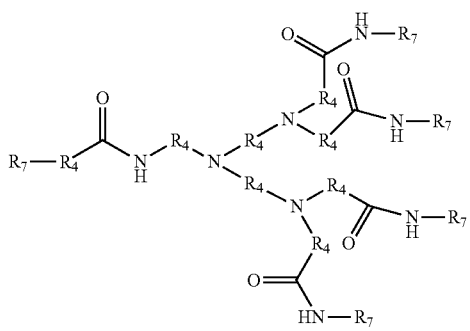

wherein $R_7$ comprises a link to a portion of a copolymer or copolymer network comprising a residue of a compound, said compound independently represented by Formula III.

In some embodiments, the present invention provides polymers, polymer networks that comprise said polymers or residues thereof, compositions that comprise polymers and/or polymer networks, and methods for removing a compound or ion, such as a phosphorous-containing compound or a phosphorous-containing ion (e.g. phosphate) from the gastrointestinal tract of an animal by administering an effective amount of a polymer or polymer network, where the polymer is derived from a vinyl amide monomer, said monomer comprising one or more vinyl groups and one or more non-amido amine groups, where the polymer has one or more of the following characteristics:

a degree of branching of from 0.10 to 0.95;
from 10-95% of the nitrogen atoms in the polymer are the nitrogen in a secondary amine moiety;
a polydispersity greater than about 1.2;
random, variable length branching;
greater than 10% and less than 90% of non-terminal, non-amido amine groups in said polymer comprise tertiary amines;
when branched, an intrinsic viscosity that has no maximum (versus viscosity averaged molecular weight).

In some embodiments, the present invention provides polymers and/or polymer networks that comprise polymers or residues thereof, compositions that comprise polymers, and/or polymer networks, and methods for removing a compound or ion, such as a phosphorous-containing compound or a phosphorous-containing ion (e.g. phosphate) from the gastrointestinal tract of an animal by administering an effective amount of a polymer or polymer network, where the polymers comprise a polymer derived from a monomer represented by the following Formula VI:

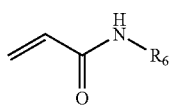

Formula VI wherein $R_6$ represents —R—$R_7$, —R—NH—R—$R_7$, —$R_8$, —R—N—$(R_8)_2$, —R—N(R—$R_7$)—$R_8$ or —R—N(R—$R_7$)—R—N($R_8$)—R—N—$(R_8)_2$; R independently represents a branched or unbranched, substituted or unsubstituted alkyl radical, for example a $C_1$ to $C_{20}$ alkyl radical, such as a $C_1$, $C_2$, $C_3$, $C_4$, $C_5$ or $C_6$ radical; $R_7$ independently represents —$NH_2$ or $NH_3{}^+Cl^-$; $R_8$ independently represents —R—N—(R—$R_7)_2$, where the polymers have one or more of the following characteristics:

a degree of branching of from 0.10 to 0.95;
from 10-95% of the nitrogen atoms in the polymer are the nitrogen in a secondary amine moiety;
a polydispersity greater than about 1.2;
random, variable length branching;
greater than 10% and less than 90% of non-terminal, non-amido amine groups in said polymer comprise tertiary amines;
when branched, an intrinsic viscosity that has no maximum (versus viscosity averaged molecular weight).

In some embodiments the polymer comprises one or more groups represented by one or more of the following Formulas VII-VIII:

Formula VII

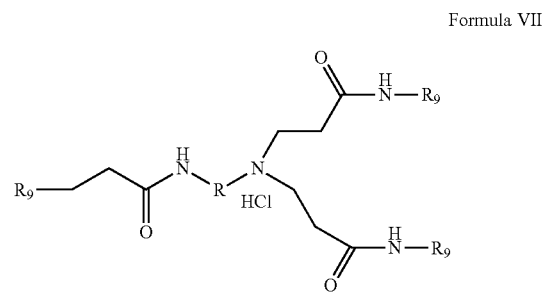

Formula VIII

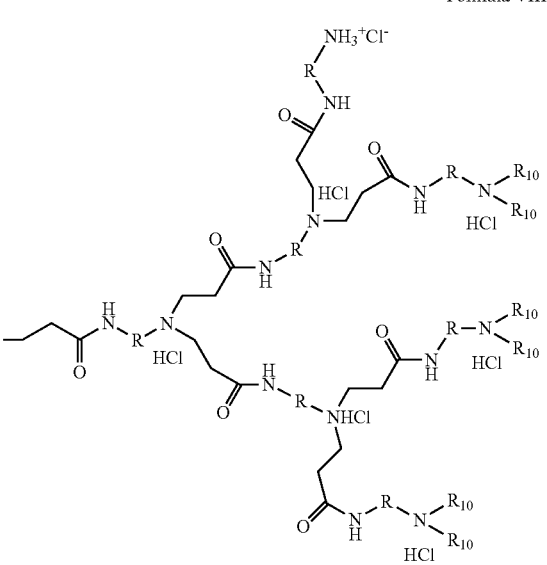

wherein $R_9$ and $R_{10}$ independently represent a link to a portion of a copolymer or copolymer network comprising a residue of a monomer, said monomer independently represented by Formula VI.

In some embodiments, the present invention provides copolymers, copolymer networks that comprise said copolymers or residues thereof, compositions that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymers comprise at least one amine compound or residue thereof, said amine compound represented by the following Formula IX:

Formula IX

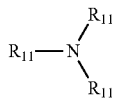

wherein $R_{11}$ independently represents a hydrogen radical or a unit independently represented by the following Formula X, with the proviso that at least one $R_{11}$ comprises a group represented by Formula X:

Formula X

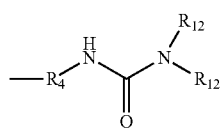

wherein $R_4$ independently represents

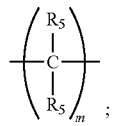

wherein m independently represents an integer from 1-20; $R_5$ independently represents a hydrogen radical; a substituted or un-substituted alkyl radical; a substituted or un-substituted aryl radical; or $R_5$ and a neighboring $R_5$ together represent a link or links comprising a residue of a crosslinking agent, a substituted or un-substituted alicyclic radical, a substituted or un-substituted aromatic radical, or a substituted or un-substituted heterocyclic radical; or $R_5$ represents a link with another compound; $R_{12}$ represents a hydrogen radical or a unit according to Formula X, where the copolymer has one or more of the following characteristics:
- a degree of branching of from 0.10 to 0.95;
- from 10-95% of the nitrogen atoms in the copolymer are the nitrogen in a secondary amine moiety;
- a polydispersity greater than about 1.2;
- random, variable length branching;
- greater than 10% and less than 90% of non-terminal, non-amido amine groups in said copolymer comprise tertiary amines;
- when branched, an intrinsic viscosity that has no maximum (versus viscosity averaged molecular weight).

In some embodiments, the present invention provides copolymers, copolymer networks that comprise said copolymers or residues thereof, compositions that comprise copolymers and/or copolymer networks, and methods for removing a compound or ion, such as a phosphorous-containing compound or a phosphorous-containing ion (e.g. phosphate) from the gastrointestinal tract of an animal by administering an effective amount of a copolymer or copolymer network, where the copolymer is derived from comonomers represented by the following Formulas I and XI:

Formula I

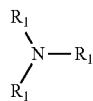

Formula XI

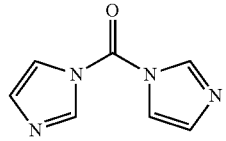

wherein $R_1$ independently represents a hydrogen radical, —$RNH_2$, —R—N—(R—$NH_2$)$_2$ or —R—N—(R—N—(R—$NH_2$)$_2$)$_2$, wherein R independently represents a branched or unbranched, substituted or unsubstituted alkyl radical, for example a $C_1$ to $C_{20}$ alkyl radical, such as a $C_1$, $C_2$, $C_3$, $C_4$, $C_5$ or $C_6$ radical, with the proviso that at least one $R_1$ is not a hydrogen radical, where the copolymer has one or more of the following characteristics:
- a degree of branching of from 0.10 to 0.95;
- from 10-95% of the nitrogen atoms in the copolymer are the nitrogen in a secondary amine moiety;
- a polydispersity greater than about 1.2;
- random, variable length branching;
- greater than 10% and less than 90% of non-terminal, non-amido amine groups in said copolymer comprise tertiary amines;
- when branched, an intrinsic viscosity that has no maximum (versus viscosity averaged molecular weight).

In some embodiments the copolymer comprises one or more groups represented by one or more of the following Formulas XII-XIII:

Formula XII

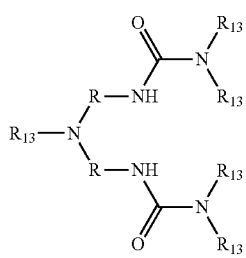

Formula XIII

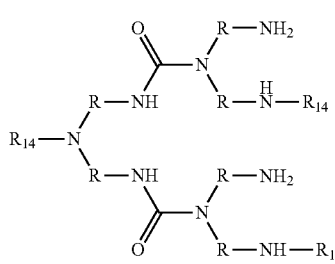

wherein $R_{13}$ and $R_{14}$ independently represent a link to a portion of a copolymer or copolymer network comprising a residue of a compound, said compound independently represented by Formula I.

In some embodiments, polymers and or copolymers of the invention may be modified with a further multi-amine post polymerization, for example by reaction of any remaining amine-reactive groups with the same or a different multi-amine.

In some embodiments, a method of making copolymers of the invention can include any suitable method such as addition of a multi-amine to a compound comprising two or more amine-reactive groups, such as an α,β-unsaturated carboxylic acid or ester, or to a multi-ester in a reactor and heating the mixture under an inert atmosphere. In some embodiments, the α,β-unsaturated carboxylic acid or ester may be an alkyl acrylate such as methyl methacrylate. In some embodiments the mixture may be heated to greater than 50° C., for example 60° C., 65° C., 70° C., 75° C., 80° C., 85° C. or higher and may be heated under a nitrogen atmosphere. In some embodiments, the mixture may be heated from 1 hour to several days, such as 1-7 days, such as from 24-72 hours. The resulting copolymer may be purified using any suitable method, such as precipitation and washing, or dialyzation. The copolymer may then be dried under vacuum or lyophilized to yield the desired copolymer.

In some embodiments, a multi-ester that may be used for making copolymers of the invention may be formed by reaction of a multi-amine with a compound comprising two or more amine-reactive groups, such as an α,β-unsaturated carboxylic acid or ester, for example an acrylate such as methyl acrylate, using any suitable technique. In some embodiments, the multi-amine may be placed in a suitable solvent, chilled to 4° C. or below, such as 4° C. to −10° C. and added to a chilled solution of the compound comprising two or more amine-reactive groups. The resulting solution may be allowed to slowly warm to room temperature and may be stirred for 1 hour to several days or a week or more at room temperature. The solution may then be washed and concentrated and dried to yield a multi-ester for use as a comonomer.

The copolymer may then be subsequently crosslinked using any suitable method. For example, the copolymer may be mixed with a crosslinking agent in a suitable solvent, such as, for example, water and stirred. A gel may form and may be cured, broken, resuspended and washed one or more times and then dried. The gel may be cured for 1 hour to 12 days, such as from 1-7 days, 2-6 days, such as 2-4 days.

In some embodiments, the invention is a method for reducing blood phosphate levels by 5-100% in a patient in need thereof, the method comprising administering a therapeutically effective amount of one or more polymers, copolymers, polymer networks and/or copolymer networks of the invention or a composition comprising one or more one or more polymers, copolymers, polymer networks and/or copolymer networks of the invention to the patient. In some embodiments, the invention is a method for reducing urinary phosphorous by 5-100% in a patient in need thereof, the method comprising administering a therapeutically effective amount of one or more polymers, copolymers, polymer networks and/or copolymer networks of the invention or a composition comprising one or more one or more polymers, copolymers, polymer networks and/or copolymer networks of the invention to the patient.

In some embodiments, the invention is a method of treating a phosphate imbalance disorder such as hyperphosphatemia comprising administering a therapeutically effective amount of one or more polymers, copolymers, polymer networks and/or copolymer networks of the invention or a composition comprising one or more one or more polymers, copolymers, polymer networks and/or copolymer networks of the invention to a patient in need thereof.

In some embodiments, the composition comprises a mixture of more than one polymer, copolymer, polymer network and/or copolymer network of the invention, for example, in some embodiments the composition comprises 2-20 such as 2, 3, 4, 5, 6, 7, 8, 9 or 10 polymers, copolymers, polymer networks and/or copolymer networks of the invention.

In some embodiments, the invention comprises a polymer, copolymer, polymer network and/or copolymer network of the invention derived from a multi-amine compound that is a mixture of multi-amine compounds, a pharmaceutical composition comprising such a polymer, copolymer, polymer network and/or copolymer network, or a method of using the same in a therapeutically effective amount to remove a compound or ion, such as a phosphorous-containing compound or a phosphorous-containing ion (e.g. phosphate), from the gastrointestinal tract of an animal.

Other embodiments of the invention include pendant polymers formed with polymers, copolymers polymer networks and/or copolymer networks as pendant groups on a polymer or polymerized backbone of a polymer. Such pendant polymers may be formed by adding one or more polymerizable groups to one or more amine groups on a polymer, copolymer, polymer network and/or copolymer network to form a pendant monomer and then subsequently polymerizing the polymerizable group to form a pendant polymer comprising a polymer, copolymer, polymer network and/or copolymer network. A schematic example of such an addition follows [it should be noted in the following that a polymer, copolymer, polymer network and/or copolymer network designated as "AC" is intended to represent a polymer, copolymer, polymer network and/or copolymer network or residue thereof, of the invention, with one of its amine groups depicted for purposes of illustrating how a polymerizable group may be added to the polymer, copolymer, polymer network and/or copolymer network]:

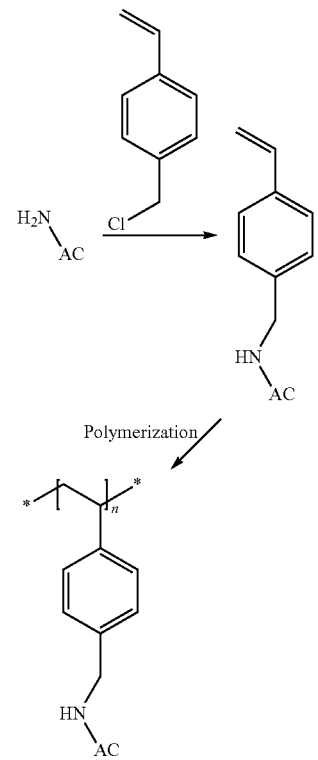

Non-limiting examples of other polymerizable groups that may be used with polymers, copolymers, polymer networks and/or copolymer network according to embodiments of the invention include:

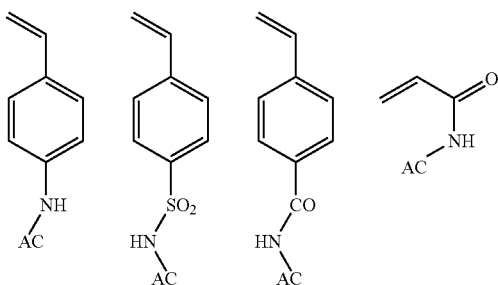

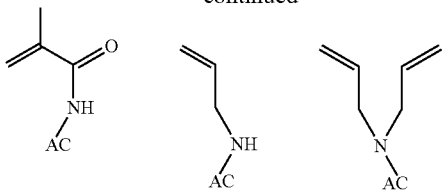

One or more polymerizable groups may be added to each AC and thus it is possible to have mixtures of pendant monomers having various pendant ACs having differing numbers of polymerizable groups. In addition, the pendant polymers made in this fashion may be modified, crosslinked, formed into a network or substituted post polymerization. Such modification may be performed for any number of reasons, including to improve efficacy, tolerability or reduce side effects.

Pendant monomers may also be formed by addition of ACs to amine-reactive polymers by reacting one or more amine groups of the ACs with one or amine-reactive groups on the amine-reactive polymers. Examples of some amine reactive polymers include:

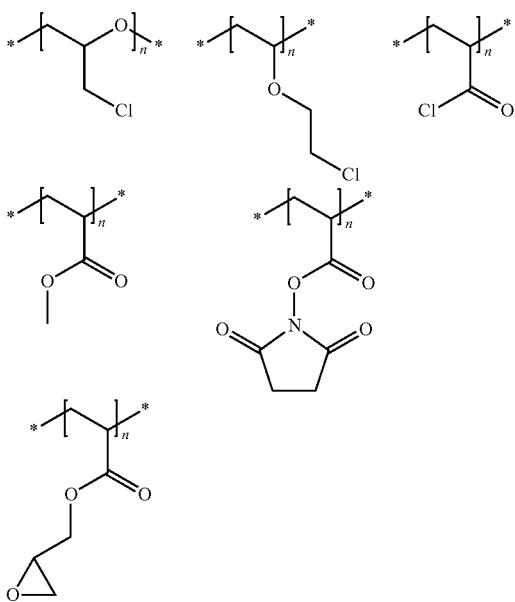

The ACs or pendant monomers may also serve as multifunctional monomers to form polymers. For example, when the ACs or the polymers formed from the pendant monomers are crosslinked, the crosslinking reaction may be carried out either in solution of bulk (i.e. using the neat amine and neat crosslinking agents) or in dispersed media. When a bulk process is used, solvents are selected so that they co-dissolve the reactants and do not interfere with the crosslinking reaction. Suitable solvents include water, low boiling alcohols (methanol, ethanol, butanol), dimethylformamide, dimethylsulfoxide, acetone, methylethylketone, and the like.

Other polymerization methods may include a single polymerization reaction, stepwise addition of individual monomers via a series of reactions, the stepwise addition of blocks of monomers, combinations of the foregoing, or any other method of polymerization, such as, for example, direct or inverse suspension, condensation, emulsion, precipitation techniques, polymerization in aerosol or using bulk polymerization/crosslinking methods and size reduction processes such as extrusion and grinding. Processes can be carried out as batch, semi-continuous and continuous processes. For processes in dispersed media, the continuous phase can be selected from apolar solvents such as toluene, benzene, hydrocarbon, halogenated solvents, supercritical carbon dioxide, and the like. With a direct suspension process, water can be used, although salt brines are also useful to "salt out" the amine and crosslinking agents in a droplet separate phase.

Polymers and copolymers, pendant monomers and pendant polymers of the invention may be copolymerized with one or more other monomers or oligomers or other polymerizable groups, may be crosslinked, may have crosslinking or other linking agents or monomers within the polymer backbone or as pendant groups or may be formed or polymerized to form a polymer network or mixed or copolymer network comprising: polymer or copolymers or residues thereof, pendant monomers or residues thereof, crosslinking agent or residues thereof, or other linking agents or residues thereof. The network may include multiple connections between the same or different molecules that may be direct or may include one or more linking groups such as crosslinking agents or other linking agents such as monomers or oligomers or residues thereof.

Non-limiting examples of comonomers which may be used alone or in combination include: styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkyl methacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl monomers and combinations thereof. Functionalized versions of these monomers may also be used. Additional specific monomers or comonomers that may be used in this invention include, but are not limited to, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-d diethylaminoethyl acrylate, triethyleneglycol acrylate, methacrylamide, N-methylacrylamide, N,N-dimethylacrylamide, N-tert-butylmethacrylamide, N—N-butylmethacrylamide, N-methylolmethacrylamide, N-ethylolmethacrylamide, N-tert-butylacrylamide, N—N-butylacrylamide, N-methylolacrylamide, N-ethylolacrylamide, 4-acryloylmorpholine, vinyl benzoic acid (all isomers), diethylaminostyrene (all isomers), α-methylvinyl benzoic acid (all isomers), diethylamino α-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylamine, methallylamine, allylalcohol, methyl-vinylether, ethylvinylether, butylvinylether, butadiene, isoprene, chloroprene, ethylene, vinyl acetate and combinations thereof.

In some embodiments, polymers and copolymers of the invention are crosslinked using crosslinking agents, and may not dissolve in solvents, and, at most, swell in solvents. The swelling ratio may be measured according to the procedure in the Test Methods section below and is typically in the range of about 1 to about 20; for example 2 to 10, 2.5 to 8, 3 to 6 such as less than 5, less than 6, or less than 7. In some embodiments, the polymers and copolymers may include crosslinking or other linking agents that may result in polymer or copolymer networks that do not form gels in solvents and may be soluble or partially soluble in some solvents.

Crosslinking agents are typically compounds having at least two functional groups that are selected from a halogen group, carbonyl group, epoxy group, ester group, acid anhydride group, acid halide group, isocyanate group, vinyl group, and chloroformate group. The crosslinking agent may be attached to the carbon backbone or to a nitrogen of an amine compound, amine monomer or residue thereof.

Examples of crosslinking agents that are suitable for synthesis of the polymers or copolymers of the present invention include, but are not limited to, one or more multifunctional crosslinking agents such as: dihaloalkanes, haloalkyloxiranes, alkyloxirane sulfonates, di(haloalkyl)amines, tri(haloalkyl)amines, diepoxides, triepoxides, tetraepoxides, bis(halomethyl)benzenes, tri(halomethyl)benzenes, tetra(halomethyl)benzenes, epihalohydrins such as epichlorohydrin and epibromohydrin poly(epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol diglycidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy)diphenylmethane, bisphenol F diglycidyl ether, 1,4-bis(2',3'-epoxypropyl)perfluoro-n-butane, 2,6-di(oxiran-2-ylmethyl)-1,2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4h-chromene-2-carboxylate, bis[4-(2,3-epoxy-propylthio)phenyl]-sulfide, 1,3-bis(3-glycidoxypropyl)tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris[[3-(epoxypropoxy)propyl]dimethylsilyloxy]-1,3,5,7,9,11,14-heptacyclopentyltricyclo[7.3.3.15,11]heptasiloxane, 4,4'-methylenebis(N,N-diglycidylaniline), bis(halomethyl)benzene, bis(halomethyl)biphenyl and bis(halomethyl)naphthalene, toluene diisocyanate, acrylol chloride, methyl acrylate, ethylene bisacrylamide, pyromellic dianhydride, succinyl dichloride, dimethylsuccinate. When the crosslinking agent is an alkylhalide compound, a base can be used to scavenge the acid formed during the reaction. Inorganic or organic bases are suitable. NaOH is preferred. The base to crosslinking agent ratio is preferably between about 0.5 to about 2.

In some embodiments, the crosslinking agents may be introduced into the polymerization reaction in an amount of from 0.5 to 25 wt. % based on the total weight of the amine polymer or polymer, such as from about 2 to about 15 wt. %, from about 2 to about 12 wt. %, from about 3 to about 10 wt. %, or from about 3 to about 6 wt. %, such as 2, 3, 4, 5, 6 wt %. The amount of crosslinking agent necessary may depend on the extent of branching within the amine compound.

In some embodiment the weight averaged molecular weight of the polymers and copolymers, may be typically at least about 1000. For example, the molecular weight may be from about 1000 to about 1,000,000, such as about 2000 to about 750,000, about 3000 to about 500,000, about 5000 to about 250,000, about 10000 to about 100,000, such as from 15,000-80,000, 20,000-75,000, 25,000 to 60,000, 30,000 to 50,000, or 40,000-45,000.

The polymers of some embodiments may be formed using a polymerization initiator. Generally, any initiator may be used including cationic and radical initiators. Some examples of suitable initiators that may be used include: the free radical peroxy and azo type compounds, such as azodiisobutyronitrile, azodiisovaleronitrile, dimethylazodiisobutyrate, 2,2'-azobis(isobutyronitrile), 2,2'-azobis(N,N-dimethyleneisobutyramidine)dihydrochloride, 2,2'-azobis(2-amidinopropane) dihydrochloride, 2,2'-azobis(N,N'-dimethyleneisobutyramidine), 1,1''-azobis(1-cyclohexanecarbo-nitrile), 4,4'-azobis(4-cyanopentanoic acid), 2,2'-azobis(isobutyramide) dihydrate, 2,2'-azobis(2-methylpropane), 2,2'-azobis(2-methylbutyronitrile), VAZO 67, cyanopentanoic acid, the peroxy pivalates, dodecylbenzene peroxide, benzoyl peroxide, di-t-butyl hydroperoxide, t-butyl peracetate, acetyl peroxide, dicumyl peroxide, cumyl hydroperoxide, dimethyl bis(butylperoxy) hexane.

In some embodiments, any of the nitrogen atoms within the polymers, copolymers, polymer networks and/or copolymer networks according to embodiments of the invention may optionally be quaternized to yield the corresponding positively charged tertiary nitrogen group, such as for example, an ammonium or substituted ammonium group. Any one or more of the nitrogen atoms in the polymers, copolymers, polymer networks and/or copolymer networks may be quaternized and such quaternization, when present, is not limited to or required to include terminal amine nitrogen atoms. In some embodiments, this quaternization may result in additional network formation and may be the result of addition of crosslinking, linking or amine reactive groups to the nitrogen. The ammonium groups may be associated with a pharmaceutically acceptable counterion.

In some embodiments, polymers, copolymers, polymer networks and/or copolymer networks or residues thereof of the invention may be partially or fully quaternized, including protonated, with a pharmaceutically acceptable counterion, which may be organic ions, inorganic ions, or a combination thereof. Examples of some suitable inorganic ions include halides (e.g., chloride, bromide or iodide) carbonates, bicarbonates, sulfates, bisulfates, hydroxides, nitrates, persulfates and sulfites. Examples of some suitable organic ions include acetates, ascorbates, benzoates, citrates, dihydrogen citrates, hydrogen citrates, oxalates, succinates, tartrates, taurocholates, glycocholates, and cholates. Preferred ions include chlorides and carbonates.

In some embodiments, polymers, copolymers, polymer networks and/or copolymer networks or residues thereof of the invention may be protonated such that the fraction of protonated nitrogen atoms is from 1 to 25%, preferably 3 to 25%, more preferably 5 to 15%.

In one embodiment, a pharmaceutically acceptable polymer, copolymer, polymer network or copolymer network or residues thereof is a polymer, copolymer, polymer network and/or copolymer network or residues thereof in protonated form and comprises a carbonate anion. In one embodiment the pharmaceutically acceptable polymer, copolymer, polymer network and/or copolymer network is in protonated form and comprises a mixture of carbonate and bicarbonate anions.

In some embodiments, polymers, copolymers, polymer networks and/or copolymer networks of the invention are characterized by their ability to bind compounds or ions. Preferably the polymers, copolymers, polymer networks and/or copolymer networks of the invention bind anions, more preferably they bind organophosphates, phosphate and/or oxalate, and most preferably they bind organophosphates or phosphate. For illustration, anion-binding polymers, copolymers, polymer networks and/or copolymer networks and especially organophosphate or phosphate-binding polymers, copolymers, polymer networks and/or copolymer networks will be described; however, it is understood that this description applies equally, with appropriate modifications that will be apparent to those of skill in the art, to other ions, compounds and solutes. Polymers, copolymers, polymer networks and/or copolymer networks may bind an ion, e.g., an anion when they associate with the ion, generally though not necessarily in a noncovalent manner, with sufficient association strength that at least a portion of the ion remains bound under the in vitro or in vivo conditions in which the polymer is used for sufficient time to effect a removal of the ion from solution or from the body. A target ion may be an ion to which the polymers, copolymers, polymer networks and/or copolymer networks binds, and usually refers to the ion whose binding to the polymers, copolymers, polymer networks and/or copolymer networks is thought to produce the therapeutic effect of the polymer, copolymer, polymer network and/or copolymer network and may be an anion or a cation. A polymer, copolymer, polymer network and/or copolymer network of the invention may have more than one target ion.

For example, some of the polymers, copolymers, polymer networks and/or copolymer networks described herein exhibit organophosphate or phosphate binding properties. Phosphate binding capacity is a measure of the amount of phosphate ion a phosphate binder can bind in a given solution. For example, binding capacities of phosphate binders can be measured in vitro, e.g., in water or in saline solution, or in vivo, e.g., from phosphate urinary excretion, or ex vivo, for example using aspirate liquids, e.g., chyme obtained from lab animals, patients or volunteers. Measurements can be made in a solution containing only phosphate ion, or at least no other competing solutes that compete with phosphate ions for binding to the polymers, copolymers, polymer networks and/or copolymer networks. In these cases, a non interfering buffer may be used. Alternatively, measurements can be made in the presence of other competing solutes, e.g., other ions or metabolites, that compete with phosphate ions (the target solute) for binding to the polymers, copolymers, polymer networks and/or copolymer networks.

Ion binding capacity for a polymer, copolymer, polymer network and/or copolymer network may be measured as indicated in the Test Methods. Some embodiments have a phosphate binding capacity which can be greater than about 0.2, 0.5, 1.0, 1.5, 2.0, 2.5, 3.0, 3.5, 4.0, 5.0, 6.0, 8.0, 10.0, 12, 14, 16, 18 or greater than about 20 mmol/g. In some embodiments, the in vitro phosphate binding capacity of polymers, copolymers, polymer networks and/or copolymer networks or residues thereof of the invention for a target ion is greater than about 0.5 mmol/g, preferably greater than about 2.5 mmol/g, even more preferably greater than about 3 mmol/g, even more preferably greater than about 4 mmol/g, and yet even more preferably greater than about 6 mmol/g. In some embodiments, the phosphate binding capacity can range from about 0.2 mmol/g to about 20 mmol/g, such as about 0.5 mmol/g to about 10 mmol/g, preferably from about 2.5 mmol/g to about 8 mmol/g, and even more preferably from about 3 mmol/g to about 6 mmol/g. Phosphate binding may be measured according to the techniques described in the Test Methods section below.

In some embodiments, polymers, copolymers, polymer networks and/or copolymer networks and compositions of the invention may reduce urinary phosphorous of a patient in need thereof by 5-100%, such as 10-75%, 25-65%, or 45-60%. Some embodiments may reduce urinary phosphorous by greater than 10%, greater than 20%, greater than 30%, greater than 40%, greater than 45%, greater than 50% or greater than 60%. Reduction of urinary phosphorous may be measured according to the methods detailed in the Test Methods section below.

In some embodiments, polymers, copolymers, polymer networks and/or copolymer networks and compositions of the invention may reduce blood phosphate of a patient in need thereof by 5-100%, such as 10-75%, 25-65%, or 45-60%. Some embodiments may reduce blood phosphate levels by greater than 10%, greater than 20%, greater than 30%, greater than 40%, greater than 45%, greater than 50% or greater than 60%.

When crosslinked, some embodiments of the amine compounds of the invention form a gel in a solvent, such as in a simulated gastrointestinal medium or a physiologically acceptable medium.

One aspect of the invention is core-shell compositions comprising a polymeric core and shell. In some embodiments, the polymeric core comprises the polymers, copolymers, polymer networks and/or copolymer networks described herein. The shell material can be chemically anchored to the core material or physically coated. In the former case, the shell can be grown on the core component through chemical means, for example by: chemical grafting of shell polymer to the core using living polymerization from active sites anchored onto the core polymer; interfacial reaction, i.e., a chemical reaction located at the core particle surface, such as interfacial polycondensation; and using block copolymers as suspending agents during the core particle synthesis.

In some embodiments, the interfacial reaction and use of block polymers are the techniques used when chemical methods are used. In the interfacial reaction pathway, typically, the periphery of the core particle is chemically modified by reacting small molecules or macromolecules on the core interface.

For example, an amine containing ion-binding core particle is reacted with a polymer containing amine reactive groups such as epoxy, isocyanate, activated esters, halide groups to form a crosslinked shell around the core.

In another embodiment, the shell is first prepared using interfacial polycondensation or solvent coacervation to produce capsules. The interior of the capsule is then filled up with core-forming precursors to build the core within the shell capsule.

In some embodiments, using the block copolymer approach, an amphiphilic block copolymer can be used as a suspending agent to form the core particle in an inverse or direct suspension particle forming process. When an inverse water-in-oil suspension process is used, then the block copolymer comprises a first block soluble in the continuous oil phase and another hydrophilic block contains functional groups that can react with the core polymer. When added to the aqueous phase, along with core-forming precursor, and the oil phase, the block copolymer locates to the water-in-oil interface and acts as a suspending agent. The hydrophilic block reacts with the core material, or co-reacts with the core-forming precursors. After the particles are isolated from the oil phase, the block copolymers form a thin shell covalently attached to the core surface. The chemical nature and length of the blocks can be varied to vary the permeation characteristics of the shell towards solutes of interest.

When the shell material is physically adsorbed on the core material, well known techniques of microencapsulation such as solvent coacervation, fluidized bed spray coater, or multi-emulsion processes can be used. One method of microencapsulation is the fluidized bed spray coater in the Wurster configuration. In yet another embodiment, the shell material is only acting temporarily by delaying the swelling of the core particle while in the mouth and esophagus, and optionally disintegrates in the stomach or duodenum. The shell is then selected in order to hinder the transport of water into the core particle, by creating a layer of high hydrophobicity and very low liquid water permeability.

In one embodiment the shell material carries negative charges while being in the milieu of use. Not being limited to one mechanism of action, it is thought that negatively charged shell material coated on anion-binding beads enhance the binding of small inorganic ions with a low charge density (such as phosphate) over competing ions with greater valency or size. Competing anions such as citrate, bile acids and fatty acids among others, may thus have a lesser relative affinity to the anion binding core possibly as a result of their limited permeability across the shell.

In some embodiments, shell materials are polymers carrying negative charges in the pH range typically found in the intestine. Examples include, but are not limited to, polymers that have pendant acid groups such as carboxylic, sulfonic, hydrosulfonic, sulfamic, phosphoric, hydrophosphoric, phosphonic, hydrophosphonic, phosphoramidic, phenolic, boronic and a combination thereof. The polymer can be protonated or unprotonated; in the latter case the acidic anion can be neutralized with pharmaceutically acceptable cations such as Na, K, Li, Ca, Mg, and $NH_4$.

In another embodiment the polyanion can be administered as a precursor that ultimately activates as a polyanion: for instance, certain labile ester or anhydride forms of either polysulfonic or polycarboxylic acids are prone to hydrolysis in the acidic environment of the stomach and can convert to the active anions.

The shell polymers can be either linear, branched, hyperbranched, segmented (i.e. backbone polymer arranged in sequence of contiguous blocks of which at least one contains pendant acidic groups), comb-shaped, star-shaped or crosslinked in a network, fully and semi-interpenetrated network (IPN). The shell polymers are either random or block in composition and either covalently or physically attached to the core material. Examples of such shell polymers include, but are not limited to acrylic acid homopolymers or copolymers, methacrylic acid homopolymers or copolymers, and copolymers of methacrylate and methacrylic acid. Examples of such polymers are copolymers of methylmethacrylate and methacrylic acid and copolymers of ethylacrylate and methacrylic acid, sold under the tradename Eudragit (Rohm GmbH & Co. KG): examples of which include Eudragit L100-55 and Eudragit L100 (a methylmethacrylate-methacrylic acid (1:1) copolymer, Degussa/Rohm), Eudragit L30-D55, Eudragit S 100-55 and Eudragit FS 30D, Eudragit S 100 (a methylmethacrylate-methacrylic acid (2:1) copolymer), Eudragit LD-55 (an ethylacrylate-methacrylic acid (1:1) copolymer), copolymers of acrylates and methacrylates with quaternary ammonium groups, sold under the tradenames Eudragit RL and Eudragit RS, and a neutral ester dispersion without any functional groups, sold under the tradename Eudragit NE30-D.

Additional shell polymers include: poly(styrene sulfonate), Polycarbophil®; polyacrylic acid(s); carboxymethyl cellulose, cellulose acetate phthalate, hydroxypropyl methylcellulose phthalate as sold under the tradename HP-50 and HP-55 (Shin-Etsu Chemical Co., Ltd.), cellulose acetate trimellitate, cellulose acetate, cellulose acetate butyrate, cellulose acetate propionate, ethyl cellulose, cellulose derivatives, such as hydroxypropylmethylcellulose, methylcelluose, hydroxylethylcellulose, hydroxyethylmethylcellulose, hydroxylethylethylcelluose and hydroxypropylethylcellulose and cellulose derivatives such as cellulose ethers useful in film coating formulations, polyvinyl acetate phthalate, carrageenan, alginate, or poly(methacrylic acid) esters, acrylic/maleic acid copolymers, styrene/maleic acid polymers, itaconic acid/acrylic copolymers, and fumaric/acrylic acid copolymers, polyvinyl acetal diethylaminoacetate, as sold under the tradename AEA (Sankyo Co., Ltd.), methylvinylether/maleic acid copolymers and shellac.

In some embodiments the shell polymers are selected amongst pharmaceutically acceptable polymers such as Eudragit L100-55 and Eudragit L100 (a methylmethacrylate-methacrylic acid (1:1) copolymer, Degussa/Rohm), Carbopol 934 (polyacrylic acid, Noveon), C-A-P NF (cellulose acetate phthalate—Eastman), Eastacryl (methacrylic acid esters—Eastman), Carrageenan and Alginate (FMC Biopolymer), Anycoat—P (Samsung Fine Chemicals—HPMC Phthalate), or Aqualon (carboxymethyl cellulose—Hercules), methylvinylether/maleic acid copolymers (Gantrez), and styrene/maleic acid (SMA).

The shell can be coated by a variety of methods. In one embodiment, the shell materials are added in the drug formulation step as an active excipient; for example, the shell material can be included in a solid formulation as a powder, which is physically blended with the organophosphate or phosphate-binding polymer and other excipients, optionally granulated, and compressed to form a tablet. Thus, in some embodiments, the shell material need not cover the core material in the drug product. For example, the acidic shell polymer may be added together with the anion binding core polymer formulated in the shape of a tablet, capsule, gel, liquid, etc, wafer, extrudates and the shell polymer can then dissolve and distribute itself uniformly as a shell coating around the core while the drug product equilibrates in the mouth, esophagus or ultimately in the site of action, i.e. the GI tract.

In some embodiments, the shell is a thin layer of shell polymer. The layer can be a molecular layer of polyanion on the core particle surface. The weight to core ratio can be between about 0.0001% to about 30%, preferably comprised between about 0.01% to about 5%, such as between about 0.1% to about 5%.

The shell polymers have a minimum molecular weight such that they do not freely permeate within the core pore volume nor elute from the core surface. In some embodiments, the molecular weight (Mw) of the shell acidic polymer is above about 1,000 g/mole, such as above about 5,000 g/mole, and or even above about 20,000 g/mole.

The anionic charge density of the shell material (as prevailing in the milieu of use) is may be between 0.5 mEq/gr to 22 mEq/gr, such as 2 mEq/gr to 15 mEq/gr. If a coating process is used to form the shell on the polymer particles as part of the manufacture of the dosage form, then procedures known from those skilled-in-the-art in the pharmaceutical industry are applicable. In one embodiment, the shell is formed in a fluidized bed coater (Wurster coater). In an alternate embodiment, the shell is formed through controlled precipitation or coacervation, wherein the polymer particles are suspended in a polymer solution, and the solvent properties are changed in such a way as to induce the polymer to precipitate onto or coat the polymer particles.

Suitable coating processes include the procedures typically used in the pharmaceutical industry. Typically, selection of the coating method is dictated by a number of parameters, that include, but are not limited to the form of the shell material (bulk, solution, emulsion, suspension, melt) as well as the shape and nature of the core material (spherical beads, irregular shaped, etc.), and the amount of shell deposited. In addition, the cores may be coated with one or more shells and may comprise multiple or alternating layers of shells.

The term "phosphate imbalance disorder" as used herein refers to conditions in which the level of phosphorus present in the body is abnormal. One example of a phosphate imbalance disorder includes hyperphosphatemia. The term "hyperphosphatemia" as used herein refers to a condition in which the element phosphorus is present in the body at an elevated level. Typically, a patient is often diagnosed with hyperphosphatemia if the blood phosphate level is, for example, above about 4.0 or 4.5 milligrams per deciliter of blood, for example above about 5.0 mg/dl, such as above about 5.5 mg/dl, for example above 6.0 mg/dl, and/or a severely impaired glomerular filtration rate such as, for example, less than about 20% of normal. The present invention may also be used to treat patients suffering from hyperphosphatemia in End Stage Renal Disease and who are also receiving dialysis treatment (e.g., hemodialysis or peritoneal dialysis).

Other diseases that can be treated with the methods, compounds, compositions, and kits of the present invention include hypocalcemia, hyperparathyroidism, depressed renal synthesis of calcitriol, tetany due to hypocalcemia, renal insufficiency, and ectopic calcification in soft tissues including calcifications in joints, lungs, kidney, conjuctiva, and myocardial tissues. Also, the present invention can be used to treat Chronic Kidney Disease (CKD), End Stage Renal Disease (ESRD) and dialysis patients, including prophylactic treatment of any of the above.

The polymers, copolymers, polymer networks and/or copolymer networks and compositions described herein can be used as an adjunct to other therapies e.g. those employing dietary control of phosphorus intake, dialysis, inorganic metal salts and/or other polymer resins.

The compositions of the present invention are also useful in removing chloride, bicarbonate, oxalate, and bile acids from the gastrointestinal tract. Polymers, copolymers, polymer networks and/or copolymer networks removing oxalate compounds or ions find use in the treatment of oxalate imbalance disorders, such as oxalosis or hyperoxaluria that increases the risk of kidney stone formation. Polymers, copolymers, polymer networks and/or copolymer networks removing chloride compounds or ions find use in treating acidosis, heartburn, acid reflux disease, sour stomach or gastritis, for example. In some embodiments, the compositions of the present invention are useful for removing fatty acids, bilirubin, and related compounds. Some embodiments may also bind and remove high molecular weight molecules like proteins, nucleic acids, vitamins or cell debris.

The present invention provides methods, pharmaceutical compositions, and kits for the treatment of animals. The term "animal" or "animal subject" or "patient" as used herein includes humans as well as other mammals (e.g., in veterinary treatments, such as in the treatment of dogs or cats, or livestock animals such as pigs, goats, cows, horses, chickens and the like). One embodiment of the invention is a method of removing phosphorous-containing compounds such as organophosphates or phosphate from the gastrointestinal tract, such as the stomach, small intestine or large intestine of an animal by administering an effective amount of at least one of the polymers, copolymers, polymer networks and/or copolymer networks described herein.

The term "treating" and its grammatical equivalents as used herein includes achieving a therapeutic benefit and/or a prophylactic benefit. By therapeutic benefit is meant eradication, amelioration, or prevention of the underlying disorder being treated. For example, in a hyperphosphatemia patient, therapeutic benefit includes eradication or amelioration of the underlying hyperphosphatemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of polymers, copolymers, polymer networks and/or copolymer networks, described herein, to a patient suffering from renal insufficiency and/or hyperphosphatemia provides therapeutic benefit not only when the patient's serum phosphate level is decreased, but also when an improvement is observed in the patient with respect to other disorders that accompany renal failure and/or hyperphosphatemia like ectopic calcification and renal osteodistrophy. For prophylactic benefit, for example, the polymers, copolymers, polymer networks and/or copolymer networks may be administered to a patient at risk of developing hyperphosphatemia or to a patient reporting one or more of the physiological symptoms of hyperphosphatemia, even though a diagnosis of hyperphosphatemia may not have been made.

The compositions may also be used to control serum phosphate in subjects with elevated phosphate levels, for example, by changing the serum level of phosphate towards a normal or near normal level, for example, towards a level that is within 10% of the normal level of a healthy patient.

Other embodiments of the invention are directed towards pharmaceutical compositions comprising at least one of the polymers, copolymers, polymer networks and/or copolymer networks or a pharmaceutically acceptable salt thereof, and one or more pharmaceutically acceptable excipients, diluents, or carriers and optionally additional therapeutic agents. The compounds may be lyophilized or dried under vacuum or oven before formulating.

The excipients or carriers are "acceptable" in the sense of being compatible with the other ingredients of the formulation and not deleterious to the recipient thereof. The formulations can conveniently be presented in unit dosage form and can be prepared by any suitable method. The methods typically include the step of bringing into association the agent with the excipients or carriers such as by uniformly and intimately bringing into association the amine polymer with the excipients or carriers and then, if necessary, dividing the product into unit dosages thereof.

The pharmaceutical compositions of the present invention include compositions wherein the polymers, copolymers, polymer networks and/or copolymer networks are present in an effective amount, i.e., in an amount effective to achieve therapeutic and/or prophylactic benefit. The actual amount effective for a particular application will depend on the patient (e.g. age, weight) the condition being treated; and the route of administration.

The dosages of the polymers, copolymers, polymer networks and/or copolymer networks in animals will depend on the disease being, treated, the route of administration, and the physical characteristics of the animal being treated. Such dosage levels in some embodiments for either therapeutic and/or prophylactic uses may be from about 1 gm/day to about 30 gm/day, for example from about 2 gm/day to about 20 gm/day or from about 3 gm/day to about 7 gm/day. The dose of the polymers, copolymers, polymer networks and/or copolymer networks described herein can be less than about 50 gm/day, less than about 40 gm/day, less than about 30 gm/day, less than about 20 gm/day, and less than about 10 gm/day.

Typically, the polymers, copolymers, polymer networks and/or copolymer networks can be administered before or after a meal, or with a meal. As used herein, "before" or "after" a meal is typically within two hours, preferably within one hour, more preferably within thirty minutes, most preferably within ten minutes of commencing or finishing a meal, respectively.

Generally, it is preferred that the polymers, copolymers, polymer networks and/or copolymer networks are administered along with meals. The polymers, copolymers, polymer networks and/or copolymer networks may be administered one time a day, two times a day, or three times a day. Preferably the polymers, copolymers, polymer networks and/or copolymer networks are administered once a day with the largest meal.

Preferably, the polymers, copolymers, polymer networks and/or copolymer networks may be used for therapeutic and/or prophylactic benefits and can be administered alone or in the form of a pharmaceutical composition. The pharmaceutical compositions comprise the polymers, copolymers, polymer networks and/or copolymer networks, one or more pharmaceutically acceptable carriers, diluents or excipients, and optionally additional therapeutic agents. For example, the polymers, copolymers, polymer networks and/or copolymer networks of the present invention may be co-administered with other active pharmaceutical agents depending on the condition being treated. Examples of pharmaceutical agents that may be co-administered include, but are not limited to:

Other phosphate sequestrants including pharmaceutically acceptable lanthanum, calcium, aluminum, magnesium and zinc compounds, such as acetates, carbonates, oxides, hydroxides, citrates, alginates, and ketoacids thereof.

Calcium compounds, including calcium carbonate, acetate (such as PhosLo® calcium acetate tablets), citrate, alginate, and ketoacids, have been utilized for phosphate binding.

Aluminium-based phosphate sequestrants, such as Amphojel® aluminium hydroxide gel, have also been used for treating hyperphosphatemia. These compounds complex with intestinal phosphate to form highly insoluble aluminium phosphate; the bound phosphate is unavailable for absorption by the patient.

The most commonly used lanthanide compound, lanthanum carbonate (Fosrenol®) behaves similarly to calcium carbonate.

Other phosphate sequestrants suitable for use in the present invention include pharmaceutically acceptable magnesium compounds. Various examples of pharmaceutically acceptable magnesium compounds are described in U.S. Provisional Application No. 60/734,593 filed Nov. 8, 2005, the entire teachings of which are incorporated herein by reference. Specific suitable examples include magnesium oxide, magnesium hydroxide, magnesium halides (e.g., magnesium fluoride, magnesium chloride, magnesium bromide and magnesium iodide), magnesium alkoxides (e.g., magnesium ethoxide and magnesium isopropoxide), magnesium carbonate, magnesium bicarbonate, magnesium formate, magnesium acetate, magnesium trisilicates, magnesium salts of organic acids, such as fumaric acid, maleic acid, acrylic acid, methacrylic acid, itaconic acid and styrenesulfonic acid, and a combination thereof.

Various examples of pharmaceutically acceptable zinc compounds are described in PCT Application No. PCT/US2005/047582 filed Dec. 29, 2005, the entire teachings of which are incorporated herein by reference. Specific suitable examples of pharmaceutically acceptable zinc compounds include zinc acetate, zinc bromide, zinc caprylate, zinc carbonate, zinc chloride, zinc citrate, zinc formate, zinc hexafluorosilicate, zinc iodate, zinc iodide, zinc iodide-starch, zinc lactate, zinc nitrate, zinc oleate, zinc oxalate, zinc oxide, calamine (zinc oxide with a small proportion of ferric oxide), zinc p-phenolsulfonate, zinc propionate, zinc salicylate, zinc silicate, zinc stearate, zinc sulfate, zinc sulfide, zinc tannate, zinc tartrate, zinc valerate and zinc ethylenebis (dithiocarbamate). Another example includes poly(zinc acrylate).

When referring to any of the above-mentioned phosphate sequestrants, it is to be understood that mixtures, polymorphs and solvates thereof are encompassed.

In some embodiments, a mixture of the phosphate sequestrants described above can be used in the invention in combination with pharmaceutically acceptable ferrous iron salts.

In other embodiments, the phosphate sequestrant used in combination with polymers, copolymers, polymer networks and/or copolymer networks of the present invention is not a pharmaceutically acceptable magnesium compound. In yet other embodiments, the phosphate sequestrant used in combination with the pharmaceutically acceptable polymers, copolymers, polymer networks and/or copolymer networks is not a pharmaceutically acceptable zinc compound.

The invention also includes methods and pharmaceutical compositions directed to a combination therapy of the polymers, copolymers, polymer networks and/or copolymer networks in combination with a phosphate transport inhibitor or an alkaline phosphatase inhibitor. Alternatively, a mixture of the polymers, copolymers, polymer networks and/or copolymer networks is employed together with a phosphate transport inhibitor or an alkaline phosphatase inhibitor.

Suitable examples of phosphate transport inhibitors can be found in co-pending U.S. Application Publication Nos. 2004/0019113 and 2004/0019020 and WO 2004/085448, the entire teachings of each of which are incorporated herein by reference.

A large variety of organic and inorganic molecules are inhibitors to alkaline phosphatase (ALP) (see, for example, U.S. Pat. No. 5,948,630, the entire teachings of which are incorporated herein by reference). Examples of alkaline phosphatase inhibitors include orthophosphate, arsenate, L-phenylalanine, L-homoarginine, tetramisole, levamisole, L-p-Bromotetramisole, 5,6-Dihydro-6-(2-naphthyl) imidazo-[2,1-b]thiazole (napthyl) and derivatives thereof. The preferred inhibitors include, but are not limited to, levamisole, bromotetramisole, and 5,6-Dihydro-6-(2-naphthyl)imidazo-[2,1-b]thiazole and derivatives thereof.

This co-administration can include simultaneous administration of the two agents in the same dosage form, simultaneous administration in separate dosage forms, and separate administration. For example, for the treatment of hyperphosphatemia, the polymers, copolymers, polymer networks and/or copolymer networks may be co-administered with calcium salts which are used to treat hypocalcemia resulting from hyperphosphatemia.

The pharmaceutical compositions of the invention can be formulated as a tablet, sachet, slurry, food formulation, troche, capsule, elixir, suspension, syrup, wafer, chewing gum or lozenge.

Preferably, the polymers, copolymers, polymer networks and/or copolymer networks or the pharmaceutical compositions comprising the polymers, copolymers, polymer networks and/or copolymer networks is administered orally. Illustrative of suitable methods, vehicles, excipients and carriers are those described, for example, in *Remington's Pharmaceutical Sciences*, 19th ed., the contents of which is incorporated herein by reference.

Pharmaceutical compositions for use in accordance with the present invention may be formulated in conventional manner using one or more physiologically acceptable carriers comprising excipients and auxiliaries which facilitate processing of the active polymers, copolymers, polymer networks and/or copolymer networks into preparations which can be used pharmaceutically. Proper formulation is dependent upon the route of administration chosen. Suitable techniques for preparing pharmaceutical compositions of the amines are well known in the art.

In some aspects of the invention, the polymers, copolymers, polymer networks and/or copolymer networks provide mechanical and thermal properties that are usually performed by excipients, thus decreasing the amount of such excipients required for the formulation. In some embodiments the polymers, copolymers, polymer networks and/or copolymer networks constitutes over about 30 wt. %, for example over about 40 wt. %, over about 50 wt. %, preferably over about 60 wt. %, over about 70 wt. %, more preferably over about 80 wt. %, over about 85 wt. % or over about 90 wt. % of the composition, the remainder comprising suitable excipient(s).

In some embodiments, the compressibility of the tablets is strongly dependent upon the degree of hydration (moisture content) of the polymers, copolymers, polymer networks and/or copolymer networks. Preferably, the polymers, copolymers, polymer networks and/or copolymer networks has a moisture content of about 5% by weight or greater, more preferably, the moisture content is from about 5% to about 9% by weight, and most preferably about 7% by weight. It is to be understood that in embodiments in which the amine polymer is hydrated, the water of hydration is considered to be a component of the amine polymer.

The tablet can further comprise one or more excipients, such as hardeners, glidants and lubricants, which are well known in the art. Suitable excipients include colloidal silicon dioxide, stearic acid, magnesium silicate, calcium silicate, sucrose, calcium stearate, glyceryl behenate, magnesium stearate, talc, zinc stearate and sodium stearyl fumarate.

The tablet core of embodiments of the invention may be prepared by a method comprising the steps of: (1) hydrating or drying the polymers, copolymers, polymer networks and/or copolymer networks to the desired moisture level; (2) blending the polymers, copolymers, polymer networks and/or copolymer networks with any excipients; and (3) compressing the blend using conventional tableting technology.

In some embodiments, the invention relates to a stable, swallowable coated tablet, particularly a tablet comprising a hydrophilic core, such as a tablet comprising the polymers, copolymers, polymer networks and/or copolymer networks, as described above. In one embodiment, the coating composition comprises a cellulose derivative and a plasticizing agent. The cellulose derivative is, preferably, hydroxypropylmethylcellulose (HPMC). The cellulose derivative can be present as an aqueous solution. Suitable hydroxypropylmethylcellulose solutions include those containing HPMC low viscosity and/or HPMC high viscosity. Additional suitable cellulose derivatives include cellulose ethers useful in film coating formulations. The plasticizing agent can be, for example, an acetylated monoglyceride such as diacetylated monoglyceride. The coating composition can further include a pigment selected to provide a tablet coating of the desired color. For example, to produce a white coating, a white pigment can be selected, such as titanium dioxide.

In one embodiment, the coated tablet of the invention can be prepared by a method comprising the step of contacting a tablet core of the invention, as described above, with a coating solution comprising a solvent, at least one coating agent dissolved or suspended in the solvent and, optionally, one or more plasticizing agents. Preferably, the solvent is an aqueous solvent, such as water or an aqueous buffer, or a mixed aqueous/organic solvent. Preferred coating agents include cellulose derivatives, such as hydroxypropylmethylcellulose. Typically, the tablet core is contacted with the coating solution until the weight of the tablet core has increased by an amount ranging from about 4% to about 6%, indicating the deposition of a suitable coating on the tablet core to form a coated tablet.

Other pharmaceutical excipients useful in the some compositions of the invention include a binder, such as microcrystalline cellulose, carbopol, providone and xanthan gum; a flavoring agent, such as mannitol, xylitol, maltodextrin, fructose, or sorbitol; a lubricant, such as vegetable based fatty acids; and, optionally, a disintegrant, such as croscarmellose sodium, gellan gum, low-substituted hydroxypropyl ether of cellulose, sodium starch glycolate. Such additives and other suitable ingredients are well-known in the art; see, e.g., Gennaro A R (ed), *Remington's Pharmaceutical Sciences*, 19th Edition.

In some embodiments the polymers, copolymers, polymer networks and/or copolymer networks of the invention are provided as pharmaceutical compositions in the form of chewable tablets. In addition to the active ingredient, the following types of excipients are commonly used: a sweetening agent to provide the necessary palatability, plus a binder where the former is inadequate in providing sufficient tablet hardness; a lubricant to minimize frictional effects at the die wall and facilitate tablet ejection; and, in some formulations a small amount of a disintegrant is added to facilitate mastication. In general excipient levels in currently-available chewable tablets are on the order of 3-5 fold of active ingredient(s) whereas sweetening agents make up the bulk of the inactive ingredients. In some embodiments the invention provides a pharmaceutical composition formulated as a chewable tablet, comprising a polymer, copolymer, polymer network and/or copolymer networks described herein, a filler, and a lubricant.

In some embodiments the invention provides a pharmaceutical composition formulated as a chewable tablet, comprising a polymer, copolymer, polymer network and/or copolymer network described herein, a filler, and a lubricant, wherein the filler is chosen from the group consisting of sucrose, mannitol, xylitol, maltodextrin, fructose, and sorbitol, and wherein the lubricant is a magnesium fatty acid salt, such as magnesium stearate.

In one embodiment, the polymer, copolymer, polymer network and/or copolymer network is pre-formulated with a high Tg/high melting point low molecular weight excipient such as mannitol, sorbose, and sucrose in order to form a solid solution wherein the polymer and the excipient are intimately mixed. Methods of mixing such as extrusion, spray-drying, chill drying, lyophilization, or wet granulation are useful. Indication of the level of mixing is given by known physical methods such as differential scanning calorimetry or dynamic mechanical analysis.

In some embodiments the polymers, copolymers, polymer networks and/or copolymer networks of the invention are provided as pharmaceutical compositions in the form of liquid formulations. In some embodiments the pharmaceutical composition contains a polymer, copolymer, polymer network and/or copolymer network dispersed in a suitable liquid excipient. Suitable liquid excipients are known in the art; see, e.g., *Remington's Pharmaceutical Sciences*.

In some embodiments, the pharmaceutical compositions may be in the form of a powder formulation packaged as a sachet that may be mixed with water or other ingestible liquid and administered orally as a drink (solution or suspension). In order to ensure that such formulations provide acceptable properties to the patient such as mouth feel and taste, a pharmaceutically acceptable anionic stabilizer may be included in the formulation.

Examples of suitable anionic stabilizers include anionic polymers such as: an anionic polypeptide, an anionic polysaccharide, or a polymer of one or more anionic monomers such as polymers of mannuronic acid, guluronic acid, acrylic acid, methacrylic acid, glucuronic acid glutamic acid or a combination thereof, and pharmaceutically acceptable salts thereof. Other examples of anionic polymers include cellulose, such as carboxyalkyl cellulose or a pharmaceutically acceptable salt thereof. The anionic polymer may be a homopolymer or copolymer of two or more of the anionic monomers described above. Alternatively, the anionic copolymer may include one or more anionic monomers and one or more neutral comonomers such as olefinic anionic monomers such as vinyl alcohol, acrylamide, and vinyl formamide.

Examples of anionic polymers include alginates (e.g. sodium alginate, potassium alginate, calcium alginate, magnesium alginate, ammonium alginate, and esters of alginate), carboxymethyl cellulose, polylactic acid, polyglutamic acid, pectin, xanthan, carrageenan, furcellaran, gum Arabic, karaya gum, gum ghatti, gum carob, and gum tragacanth. Preferred anionic polymers are alginates and are preferably esterified alginates such as a C2-C5-diol ester of alginate or a C3-C5 triol ester of alginate. As used herein an "esterified alginate" means an alginic acid in which one or more of the carboxyl groups of the alginic acid are esterified. The remainder of the carboxylic acid groups in the alginate are optionally neutralized (partially or completely) as pharmaceutically acceptable salts. For example, propylene glycol alginate is an ester of alginic acid in which some of the carboxyl groups are esterified with propylene glycol, and the remainder of the carboxylic acid groups is optionally neutralized with pharmaceutically acceptable salts. More preferably, the anionic polymer is ethylene glycol alginate, propylene glycol alginate or glycerol alginate, with propylene glycol alginate even more preferred.

All publications and patent applications mentioned in this specification are herein incorporated by reference to the same extent as if each individual publication or patent application was specifically and individually indicated to be incorporated by reference.

It will be apparent to one of ordinary skill in the art that many changes and modification can be made to the disclosures presented herein without departing from the spirit or scope of the appended claims.

EXAMPLES

As used herein, the following terms have the meanings ascribed to them unless specified otherwise: DAB-4-1,4-bis[bis(3-aminopropyl)amino]butane, commercially available from Aldrich.

Materials Used

Dichloromethane, diethyl ether, epichlorohydrin, methanol, methylene chloride, methyl acrylate, tert-butyl methyl ether, tris(3-aminopropyl)amine and tris(2-aminoethyl)amine are commercially available from Sigma-Aldrich, Co.

Example 1

Synthesis of Compound I 2.5 g of a chilled solution (2° C.) of tris(3-aminopropyl)amine in 2.5 ml of anhydrous methanol was added to an ice water bath chilled solution (2° C.) of 8.7 ml of methyl acrylate in 10 ml of anhydrous methanol. The solution was allowed to slowly warm to room temperature and was stirred six days at room temperature. The solution was concentrated on a rotary evaporator (bath temperature at 40° C.) yielding a light-yellow colored viscous oil. 50 ml of anhydrous methanol was added to this material and the solution was concentrated on a rotary evaporator (bath temperature 40° C.). The addition of anhydrous methanol (40 ml) and concentration on a rotary evaporator was repeated two additional times. The resulting material was dried in vacuo yielding 9.15 g of viscous oil.

Example 2

Synthesis of Compound II 10 g of a chilled solution (2° C.) of tris(2-aminoethyl)amine in 10 ml of anhydrous methanol was slowly added to an ice water bath chilled solution (0° C.) of 45 ml of methyl acrylate in 40 ml of anhydrous methanol. The solution was allowed to slowly warm to room temperature and stirred for six days at room temperature. The solution was concentrated on a rotary evaporator (bath temperature 40° C.) to yield a light yellow viscous oil. 50 ml of anhydrous methanol was added to this material and the solution was concentrated on a rotary evaporator (bath temperature 40° C.). The addition of anhydrous methanol (40 ml) and concentration on a rotary evaporator was repeated two additional times. The resulting material was dried in vacuo.

Example 3

Synthesis of Compound III 10 g of a chilled solution (2° C.) of DAB-4 in 10 ml of anhydrous methanol was slowly added to an ice water bath chilled solution (0° C.) of 28 ml of methyl acrylate in 28 ml of anhydrous methanol. The solution was allowed to slowly warm to room temperature and stirred for five days at room temperature. The solution was concentrated on a rotary evaporator (bath temperature 40° C.) to afford a light yellow colored viscous oil. 50 ml of anhydrous methanol was added to this material and the solution was concentrated on a rotary evaporator (bath temperature 40° C.). The addition of anhydrous methanol (40 ml) and concentration on a rotary evaporator was repeated two additional times. The resulting material was dried in vacuo to afford 30.11 g of the desired product.

Example 4

Synthesis of Compound IV

A mixture of 10 g of Compound I and 28.92 g of tris(3-aminopropyl)amine was heated at 75° C. for four days under a nitrogen atmosphere. The mixture was cooled to room temperature, 50 ml of methanol was added to the reaction mixture, and the resulting solution was slowly added, with stirring to 2 L of diethylether. The solution was allowed to settle, the solvent (mostly diethyl ether) was decanted from the precipitate, and the precipitate was dried in a vacuum oven at 30° C. The dried material was re-dissolved in methylene chloride and concentrated on a rotary evaporator (bath temperature 45° C.) in vacuo. A stream of nitrogen was blown over the residue overnight to yield 22.72 g of the desired product.

Example 5

Reaction of Compound IV with Epichlorohydrin

A mixture of 19.40 g of Compound IV and 19.04 g of deionized water was heated at 60° C. until a solution formed. 905 ul of epichlorohydrin was added to a 19.04 g aliquot of this solution. Within ten minutes of stirring at room temperature, a gel formed and was cured overnight at room temperature. After curing, the gel was broken into small pieces, suspended in 1 L of deionized water and the pH of the suspension was adjusted to 7.6 using concentrated HCl. The suspension was filtered, and the collected material was re-suspended in 1 L of deionized water, stirred and filtered. The resulting material, having a wet weight of 142 g, was dried in a forced air oven at 60° C. to afford 8.1 g of desired product having an In-Process Swelling Ratio of 16 ml/g.

Example 6

Reaction of Compound IV with Epichlorohydrin 1.07 ml of epichlorohydrin was added to a solution of 7.5 g of Compound IV in 7.5 g of water. Within ten minutes of stirring at room temperature, a gel formed and was cured over night at room temperature. After curing, the gel was broken into small pieces, suspended in 1 L of deionized water and the pH of the suspension was adjusted to 8 using concentrated HCl. The suspension was filtered, and the collected material was re-suspended in 1 L of deionized water, stirred and filtered. The resulting material, having a wet weight of 48 g, was dried in a forced air oven at 60° C. to afford 5.9 g of desired product having an In-Process Swelling Ratio of 7.1 ml/g.

Example 7

Reaction of Compound IV with Epichlorohydrin

Epichlorohydrin was added to a solution of Compound IV in water and cured for different periods of time according to the amounts and times in Table I below. After curing, the gel was broken into small pieces, suspended in 200 ml of deionized water, stirred, pH adjusted to 7.0 using concentrated HCL, and filtered. The material was dried in a forced air oven at 60° C. The results are summarized in Table I below.

TABLE I

Reaction of Compound IV with Epichlorohydrin

| Example | Amount of Compound IV (g) | Amount of DI water (g) | Amount of Epichlorohydrin (ul) | Curing Conditions | Yield (g) | In-Process Swelling (ml/g) |
|---|---|---|---|---|---|---|
| VII-1 | 0.787 | 0.788 | 28 | 1 day at room temperature, 3 days at 60° C. | 0.1 | 33.5 |
| VII-2 | 0.734 | 0.749 | 42 | 30 minutes at room temperature, 1 day at 60° C. | 0.5 | 41 |
| VII-3 | 0.836 | 0.844 | 64 | 30 minutes at room temperature, 1 day at 60° C. | 0.68 | 22 |

Example 8

Synthesis of Compound VIII

A mixture of 10 g of Compound I and 21.3 ml of tris(2-aminoethyl)amine was heated at 75° C. for four days under a nitrogen atmosphere. The mixture was cooled to room temperature, 30 ml of dichloromethane was added to the reaction mixture, and the resulting solution was slowly added, with stirring to 2 L of diethylether. The solution was allowed to settle for 30 minutes, the solvent (mostly diethyl ether) was decanted from the precipitate. The precipitate was dissolved in methylene chloride with a little methanol, and concentrated on a rotary evaporator (bath temperature 45° C.). A stream of nitrogen was blown over the residue overnight to yield 23.89 g of the desired product.

Example 9

Reaction of Compound VIII with Epichlorohydrin

Epichlorohydrin was added to a solution of Compound VIII in water and cured for different periods of time according to the amounts and times in Table II below. After curing, the gel was broken into small pieces, suspended in 200 ml of deionized water, stirred, pH adjusted to 7.0 using concentrated HCL, and filtered. The material was then dried in a forced air oven at 60° C. The results are summarized in Table II below.

TABLE II

Reaction of Compound VIII with Epichlorohydrin

| Example | Amount of Compound VIII (g) | Amount of DI water (g) | Amount of Epichlorohydrin (ul) | Curing Conditions | Yield (g) | In-Process Swelling (ml/g) |
|---|---|---|---|---|---|---|
| IX-1 | 0.75 | 0.75 | 63.2 | 1 day at room temperature | 0.62 | 18 |
| IX-2 | 0.75 | 0.75 | 84.2 | 1 day at room temperature | 0.70 | 9.9 |
| IX-3 | 0.75 | 0.75 | 105.3 | 1 day at room temperature | 0.74 | 8 |

Example 10

Reaction of Compound VIII with Epichlorohydrin 1.07 ml of Epichlorohydrin was added to a stirred solution of 9.5 g of Compound VIII in 9.5 g of deionized water. With 20 minutes of stirring at room temperature, a gel formed and was cured for three days at room temperature. After curing, the gel was broken into pieces, suspended in 1 L of deionized water and the pH of the suspension was adjusted to 8.4 using concentrated HCl. The suspension was filtered and the collected material was resuspended in 1 L of water, stirred and filtered. The resulting material, having a wet weight of 149 g, was dried in a forced air oven at 60° C. to yield 7.9 g of the desired product having an In-Process Swelling Ratio of 18 ml/g.

Example 11

Reaction of Compound VIII with Epichlorohydrin 1.605 ml of epichlorohydrin was added to a stirred solution of 9.5 g of Compound VIII in 9.5 g of deionized water. Within 23 minutes of stirring at room temperature, a gel formed and was cured for three days at room temperature. After curing, the gel was broken into small pieces, suspended in 1 L of deionized water, adjusted to pH 13 with the addition of 50% NaOH, and then further adjusted down to a pH of approximately 8-9 using concentrated HCl. The suspension was filtered, and the collected material was re-suspended in 1 L of deionized water, stirred and filtered. The resulting material, having a wet weight of 72.82 g, was dried in a forced air oven at 60° C. to afford 9.78 g of desired product having an In-Process Swelling Ratio of 6.44 ml/g.

Example 12

Synthesis of Compound XII

A mixture of 9.06 g of Compound I and 25.5 ml of tris(3-aminopropyl)amine was heated at 75° C. for 48 hours under a nitrogen atmosphere. The mixture was cooled to room temperature, 30 ml of dichloromethane was added to the mixture and the resulting solution was slowly added with stirring to 1 L of tert-butyl methyl ether. The solution was stirred for five minutes, allowed to settle at 0° C., and the solvent (mostly tert-butyl methyl ether) was decanted from the precipitate. The precipitate was mixed in methylene chloride, and concentrated on a rotary evaporator (bath temperature 40° C.) under vacuum. The concentrated material was further dried overnight under vacuum, and a stream of nitrogen was blown over the residue overnight to yield 25.57 g of the desired product. This material was subsequently dissolved in 25.57 g of deionized water to afford a 50% (w/w) stock solution.

Example 13

Reaction of Compound XII with Epichlorohydrin 1.81 ml of epichlorohydrin was added to 19 g of the 50% stock solution from Example 12. Within five minutes of stirring at room temperature, a gel formed and was cured over two nights at room temperature. After curing, the gel was broken into small pieces, suspended in 1 L of deionized water and the pH of the suspension was adjusted to 8 using concentrated HCl. The suspension was filtered, and the collected material was re-suspended in 1 L of deionized water, stirred and filtered. The resulting material, having a wet weight of 38.85 g, was dried in a forced air oven at 60° C. to afford 10.14 g of desired product having an In-Process Swelling Ratio of 2.83 ml/g.

Example 14

Reaction of Compound XII with Epichlorohydrin 905 ul of epichlorohydrin was added to 19 g of the 50% stock solution from Example 12. Within 15 minutes of stirring at room temperature, a gel formed and was cured for ten days at room temperature. After curing, the gel was broken into small pieces, suspended in 1 L of deionized water and the pH of the suspension was adjusted to 8 using concentrated HCl. The suspension was filtered, and the collected material was re-suspended in 1 L of deionized water, stirred and filtered. The resulting material, having a wet weight of 58.55 g, was dried in a forced air oven at 60° C. to afford 8.65 g of desired product having an In-Process Swelling Ratio of 5.77 ml/g.

Example 15

Synthesis of Compound XV

A mixture of 9.03 g of Compound I and 19.2 ml of tris(2-aminoethyl)amine was heated at 75° C. for 48 hours under a nitrogen atmosphere. The mixture was cooled to room temperature, 30 ml of dichloromethane was added to the mixture and the resulting solution was slowly added with stirring to 2 L of tert-butyl methyl ether. The solution was stirred for five minutes, allowed to settle at 0° C., and the solvent (mostly tert-butyl methyl ether) was decanted from the precipitate. The precipitate was mixed with methylene chloride, and concentrated on a rotary evaporator (bath temperature 40° C.) under vacuum. The concentrated material was further dried overnight in vacuo, and a stream of nitrogen was blown over the residue overnight to yield 23.12 g of the desired product. This material was subsequently dissolved in 23.12 g of deionized water to afford a 50% (w/w) stock solution.

Example 16

Reaction of Compound XV with Epichlorohydrin 2.14 ml of epichlorohydrin was added to 19 g of the 50% stock solution from Example 15. Within ten minutes of stirring at room temperature, a gel formed and was cured for two days at room temperature. After curing, the gel was broken into small pieces, suspended in 1 L of deionized water and stirred at room temperature. The suspension was filtered, and the collected material was re-suspended in 1 L of deionized water, stirred and filtered. The resulting material, having a wet weight of 50.24 g, was dried in a forced air oven at 60° C. to afford 9.86 g of desired product having an In-Process Swelling Ratio of 4.10 ml/g.

Example 17

Reaction of Compound XV with Epichlorohydrin 1070 ul of epichlorohydrin was added to 19 g of the 50% stock solution from Example 15. Within 27 minutes of stirring at room temperature, a gel formed and was cured for two days at room temperature. After curing, the gel was broken into small pieces, suspended in 1 L of deionized water and the suspension was adjusted to pH 8 using concentrated HCl. The suspension was filtered, and the collected material was re-suspended in 1 L of deionized water, stirred and filtered. The resulting material, having a wet weight of 111.22 g, was dried in a forced air oven at 60° C. to afford 7.32 g of desired product having an In-Process Swelling Ratio of 14.19 ml/g.

Example 18

Synthesis of Compound XVIII

A mixture of 9.04 g of Compound II and 20.4 ml of tris(2-aminoethyl)amine was heated at 75° C. for 48 hours under a nitrogen atmosphere. The mixture was cooled to room temperature, 30 ml of dichloromethane was added to the mixture and the resulting solution was slowly added with stirring to 2 L of tert-butyl methyl ether. The solution was stirred for five minutes, allowed to settle, the solvent (mostly tert-butyl methyl ether) was decanted from the precipitate and the precipitate was dried in vacuo overnight. The dried material was re-dissolved in methylene chloride and methanol and concentrated on a rotary evaporator (bath temperature 40° C.) under vacuum. The concentrated material was further dried overnight in vacuo, and a stream of nitrogen was blown over the residue overnight to yield 25.62 g of the desired product. This material was subsequently dissolved in 25.62 g of deionized water to afford a 50% (w/w) stock solution.

Example 19

Reaction of Compound XVIII with Epichlorohydrin 1.5 ml of epichlorohydrin was added to 26 g of the 50% stock solution from Example 18. Within one hour and 40 minutes of stirring at room temperature, a gel formed and was cured for four days at room temperature. After curing, the gel was broken into small pieces, suspended in 2 L of deionized water and stirred at room temperature. The suspension was filtered, and the collected material was re-suspended in 2 L of deionized water, stirred and filtered. The resulting material, having a wet weight of 138.3 g, was dried in a forced air oven at 60° C. to afford 9.50 g of desired product having an In-Process Swelling Ratio of 13.56 ml/g.

Example 20

Synthesis of Compound XX

A mixture of 9.03 g of Compound II and 27 ml of tris(3-aminopropyl)amine was heated at 75° C. for 48 hours under a nitrogen atmosphere. The mixture was cooled to room temperature, 30 ml of dichloromethane was added to the mixture and the resulting solution was slowly added with stirring to 2 L of tert-butyl methyl ether. The solution was stirred for five minutes, allowed to settle, the solvent (mostly tert-butyl methyl ether) was decanted from the precipitate and the precipitate was dried in a vacuum oven overnight. The dried material was re-dissolved in methylene chloride and methanol and concentrated on a rotary evaporator (bath temperature 40° C.) in vacuo. The concentrated material was further dried overnight in vacuo, and a stream of nitrogen was blown over the residue overnight to yield 28.31 g of the desired product. This material was subsequently dissolved in 28.31 g of deionized water to afford a 50% (w/w) stock solution.

Example 21

Reaction of Compound XX with Epichlorohydrin 1.2 ml of epichlorohydrin was added to 22 g of the 50% stock solution from Example 20. Within 12 minutes of stirring at room temperature, a gel formed and was cured for four days at room temperature. After curing, the gel was broken into small pieces, suspended in 2 L of deionized water and stirred at room temperature. The suspension was filtered, and the collected material was re-suspended in 2 L of deionized water, stirred and filtered. The resulting material, having a wet weight of 63.71 g, was dried in a forced air oven at 60° C. to afford 9.0 g of desired product having an In-Process Swelling Ratio of 6.08 ml/g.

Example 22

Synthesis of Compound XXII

A mixture of 9.09 g of Compound II and 45 ml of DAB-4 was heated at 75° C. for four days under a nitrogen atmosphere. The mixture was cooled to room temperature, 30 ml of dichloromethane was added to the mixture and the resulting solution was slowly added with stirring to 2 L of tert-butyl methyl ether. The solution was stirred for five minutes, allowed to settle, the solvent (mostly tert-butyl methyl ether) was decanted from the precipitate and the precipitate was dried in a vacuum oven overnight. The dried material was re-dissolved in methylene chloride and methanol and concentrated on a rotary evaporator (bath temperature 40° C.) in vacuo. The concentrated material was further dried overnight in vacuo, and a stream of nitrogen was blown over the residue overnight to yield 49.40 g of the desired product. This material was subsequently dissolved in 49.40 g of deionized water to afford a 50% (w/w) stock solution.

Example 23

Reaction of Compound XXII with Epichlorohydrin 1.5 ml of epichlorohydrin was added to 36.2 g of the 50% stock solution from Example 22. Within 11 minutes of stirring at room temperature, a gel formed and was cured for four days at room temperature. After curing, the gel was broken into small pieces, suspended in 2 L of deionized water and stirred at room temperature. The suspension was filtered, and the collected material was re-suspended in 2 L of deionized water, stirred and filtered. The resulting material, having a wet weight of 58.78 g, was dried in a forced air oven at 60° C. to afford 10.0 g of desired product having an In-Process Swelling Ratio of 4.88 ml/g.

Example 24

Synthesis of Compound XXIV

A mixture of 9.05 g of Compound I and 42 ml of DAB-4 was heated at 75° C. for four days under a nitrogen atmosphere. The mixture was cooled to room temperature, 30 ml of dichloromethane was added to the mixture and the resulting solution was slowly added with stirring to 2 L of tert-butyl methyl ether. The solution was stirred for five minutes, allowed to settle, the solvent (mostly tert-butyl methyl ether) was decanted from the precipitate and the precipitate was dried in a vacuum oven overnight. The dried material was re-dissolved in methylene chloride and methanol and concentrated on a rotary evaporator (bath temperature 40° C.) in vacuo. The concentrated material was further dried overnight in vacuo, and a stream of nitrogen was blown over the residue overnight to yield 29.58 g of the desired product. This material was subsequently dissolved in 29.58 g of deionized water to afford a 50% (w/w) stock solution.

Example 25

Reaction of Compound XXIV with Epichlorohydrin 1.3 ml of epichlorohydrin was added to 39.82 g of the 50% stock solution from Example 23. Within 19 minutes of stirring at room temperature, a gel formed and was cured for four days at room temperature. After curing, the gel was broken into small pieces, suspended in 2 L of deionized water and stirred at room temperature. The suspension was filtered, and the collected material was re-suspended in 2 L of deionized water, stirred and filtered. The resulting material, having a wet weight of 71.4 g, was dried in a forced air oven at 60° C. to afford 10.5 g of desired product having an In-Process Swelling Ratio of 5.8 ml/g

Example 26

Synthesis of Compound XXVI

A mixture of Compound III (29.54 g) and tris(2-aminoethyl)amine (60.0 mL) was heated at 75° C. for four days under a nitrogen atmosphere. The resulting solution was diluted with deionized water and dialyzed against deionized water (membrane MWCO 3,500). The dialyzed solution was concentrated and lyophilized to afford 34.16 g.

Example 27

Reaction of Compound XXVI with Epichlorohydrin 2.0 ml of epichlorohydrin was added to 17.25 g of a 50% (w/w) aqueous solution of Compound XXVI. Within 14 minutes of stirring at room temperature, a gel formed and was cured overnight at room temperature and for 8 hours at 60° C. After curing and cooling to room temperature, the gel was broken into small pieces, and suspended in 2 L of deionized water. The suspension was filtered, and the collected material was re-suspended in 2 L of deionized water, stirred and the pH was adjusted to 11 with 50% aqueous NaOH. This suspension was filtered, washed and filtered two more times with 2 L of deionized water each time. The resulting material having a wet weight of 74.5 g was dried in a forced air oven at 60° C. to afford 16.87 g of desired product having an In-Process Swelling of 3.42 ml/g.

Example 28

Synthesis of Compound XXVIII

A mixture of 30 g of Compound I and 64 ml of tris(2-aminoethyl)amine was heated at 75° C. for 48 hours. The mixture was cooled to room temperature, diluted with deionized water to 25% (w/w) and dialyzed (MWCO 3500). Lyophilization of the dialyzed product afforded 32.47 g of the desired product.

Example 29

Reaction of Compound XXVIII with Epichlorohydrin 3.1 ml of epichlorohydrin was added to 55.16 g of a 50% (w/w) aqueous solution of Compound XXVIII. Within 17 minutes of stirring at room temperature, a gel formed and was cured overnight at room temperature. After curing, the gel was broken into small pieces, and suspended in 2 L of deionized water. The suspension was filtered, and the collected material was re-suspended in 2 L of deionized water, stirred and filtered. The resulting material having a wet weight of 182.69 g was dried in a forced air oven at 60° C. to afford 27.79 g of desired product having an In-Process Swelling of 5.57 ml/g.

Example 30

Urinary Phosphorous Reduction (In-Vivo Rats)

Reduction of urinary phosphorous of the compounds from Example 5 and Example 10 was compared to a cellulose control and to Sevelamer in rats according to the method described in the test methods. Table III details the doses studied and the results obtained.

TABLE III

| Test Article | Dose of Test Article in Feed (% by weight in feed) | 24 Hour Urine Phosphorous (mg/day) | % Reduction in Urinary Phosphorous Study #1 |
|---|---|---|---|
| Cellulose | 0.50% | 18.1 | NA |
| Sevelamer | 0.50% | 8.3 | 54.1% |
| Example 5 Compound | 0.5% | 9.4 | 48.1 |
| Example 10 Compound | 0.5% | 7.0 | 61.3% |

Test Methods

Amine Polymer Urinary Phosphorous Reduction (In Vivo-Rats)

House male Sprague Dawley (SD) rats were used for the experiments. The rats were placed singly in wire-bottom cages, fed with Purina 5002 diet, and allowed to acclimate for at least five days prior to experimental use.

To establish baseline phosphorus excretion, the rats were placed in metabolic cages for 48 hours. Their urine was collected and its phosphorus content analyzed with a Hitachi analyzer to determine phosphorus excretion in mg/day. Any rats with outlying values were excluded; the remainder of the rats were distributed into groups.

Purina 5002 was used as the standard diet. The amine polymer being tested was mixed with Purina 5002 to result in a final amine polymer concentration of 0.25% by weight of the feed. Cellulose at 0.5% by weight was used as a negative control. Sevelamer at 0.5% by weight was used as a positive control. For each rat, 200 g of diet was prepared.

Each rat was weighed and placed on the standard diet. After four days, the standard diet was replaced with the treatment diet (or control diet for the control group). On days 5 and 6, urine samples from the rats at 24 hours (+/−30 minutes) were collected and analyzed. The test rats were again weighed, and any weight loss or gain was calculated. Any remaining food was also weighed to calculate the amount of food consumed per day. A change in phosphorus excretion relative to baseline and cellulose negative control was calculated. Percentage reduction of urinary phosphorous was determined by the following equation:

% Reduction of Urinary Phosphorous=[(urinary phosphorous of negative control (mg/day)−urinary phosphorous of experimental (mg/day))/urinary phosphorous of negative control (mg/day)]×100.

In Vitro Phosphate Binding (mmol/g)

Two samples per polymer are weighed into plastic bottles after having adjusted the weight of the polymer for the loss on drying of each sample. A 10 mM phosphate buffer solution containing 10 mM $KH_2PO_4$, 100 mM N,N-bis[2-hydroxyethyl]-2-aminoethanesulfonic acid, 80 mM NaCl, 15 mM glycochenodeoxycholic acid (GCDC), and 15 mM oleic acid (pH adjusted to 7.0 with 1 N NaOH) is prepared and well mixed. Aliquots of the 10 mM phosphate buffer solution are transferred into each of the two sample bottles. The solutions are well mixed and then placed into an orbital shaker at 37° C. for 1 hour. The polymer is allowed to settle prior to removing a sample aliquot from each solution. The sample aliquot is filtered into a small vial using a disposable syringe and syringe filter. The filtered sample is diluted 1-to-10 with DI water. The shaking is continued for a further 4 hours (total of 5 hours) and the sampling procedure is repeated. Phosphate standards are prepared from a 10 mM phosphate standard stock solution and diluted appropriately to provide standards in the range of 0.3 to 1.0 mM. Both the standards and samples are analyzed by ion chromatography. A standard curve is set up and the unbound phosphate (mM) for each test solution is calculated. Bound phosphate is determined by the following equation:

Bound Phosphate (mmol/g)=[(10−Unbound $PO_4$)× Vol.×1000]/Mass$P$; wherein Vol.=volume of test solution (L); Mass$P$=LOD adjusted mass of polymer (mg).

In-Process Swelling Ratio (mL/g)

The in-process swelling ratio (SR) is determined by the following equation:

SR=(weight of wet gel (g)−weight of dry polymer (g))/weight of dry polymer (g).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of removing a compound or ion from the gastrointestinal tract of an animal comprising administering to the animal an effective amount of a pharmaceutical composition comprising:

a) a copolymer derived from compounds according to the following Formulas I and II:

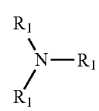

Formula I

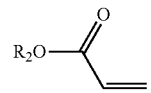

Formula II wherein R1 independently represents a hydrogen radical —$RNH_2$, —R—N—(R—$NH_2$)$_2$ or —R—N—(R—N—(R—$NH_2$)$_2$)$_2$, wherein R independently represents a branched or unbranched, substituted or unsubstituted alkyl radical, with the proviso that at least one $R_1$ is not a hydrogen radical;

$R_2$ independently represents a hydrogen radical or a branched or unbranched, substituted or unsubstituted alkyl radical; and b) a pharmaceutically acceptable excipient.

2. A method of removing a compound or ion from the gastrointestinal tract of an animal comprising administering to the animal an effective amount of a pharmaceutical composition comprising:

a) a hyperbranched copolymer derived from:
(i) a multi-amine monomer; and
(ii) a multifunctional monomer comprising two or more amine-reactive groups; and b) a pharmaceutically acceptable excipient.

3. A method of removing a compound or ion from the gastrointestinal tract of an animal comprising administering to the animal a pharmaceutical composition comprising:

a) a copolymer comprising
i) at least one multi-amine or residue thereof; and
ii) at least one ester or multi-ester or residue thereof;
wherein said copolymer has a degree of branching of from 0.10 to 0.95; and b) a pharmaceutically acceptable excipient.

4. The method of claim 2, wherein the amine reactive groups are independently selected from the group consisting of vinyl groups, carboxylic acid groups, ester groups and/or combinations thereof.

5. The method of claim 2, wherein the multifunctional monomer is selected from the group consisting of:

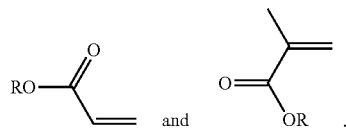

6. The method of claim 1, wherein said copolymer has a degree of branching of from 0.10 to 0.95.

7. The method of claim 1, wherein from 10-95% of the nitrogen atoms in the copolymer are the nitrogen in a secondary amine moiety.

8. The method of claim 1, wherein said copolymer has a polydispersity greater than about 1.2.

9. The method of claim 1, wherein the intrinsic viscosity of said branched copolymer has no maximum (versus viscosity averaged molecular weight).

10. The method of claim 1, wherein said copolymer has random, variable length branching.

11. The method of claim 1, wherein the compound according to Formula I is selected from the group consisting of:

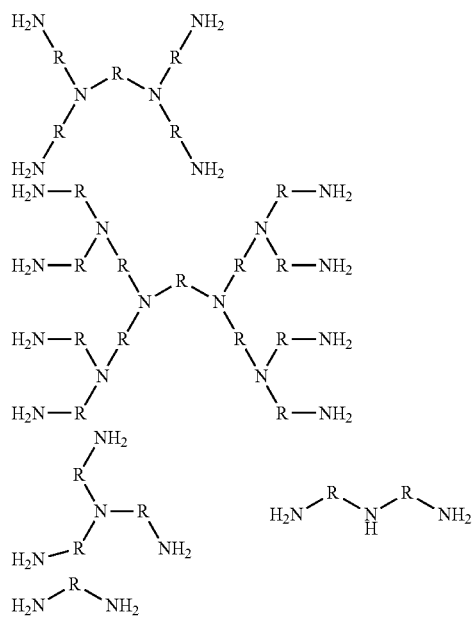

and combinations thereof, wherein R independently represents a branched or unbranched, substituted or unsubstituted alkyl radical.

12. The method of claim 1, wherein the compound according to Formula I is selected from the group consisting of:

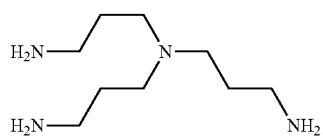

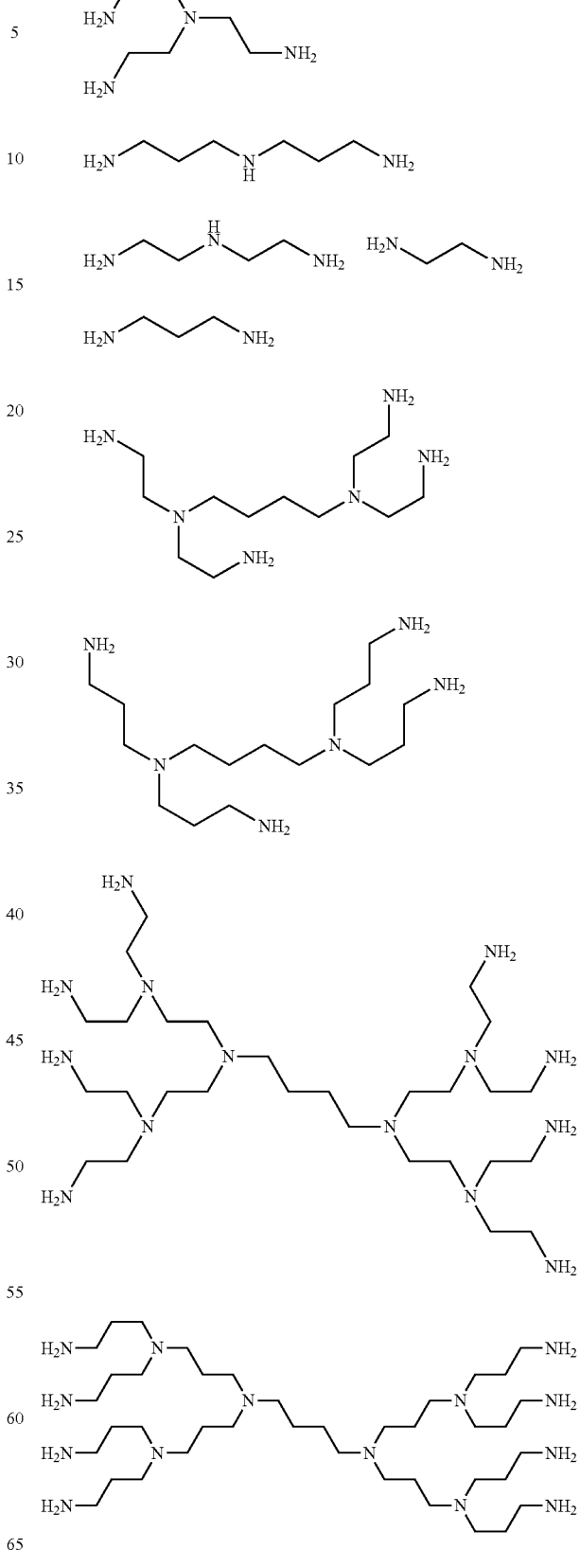

and combinations thereof.

13. The method of claim 1, wherein the compound according to Formula II is selected from the group consisting of:

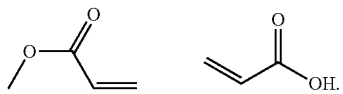

14. The method of claim 2, wherein the multi-amine is selected from the group consisting of:

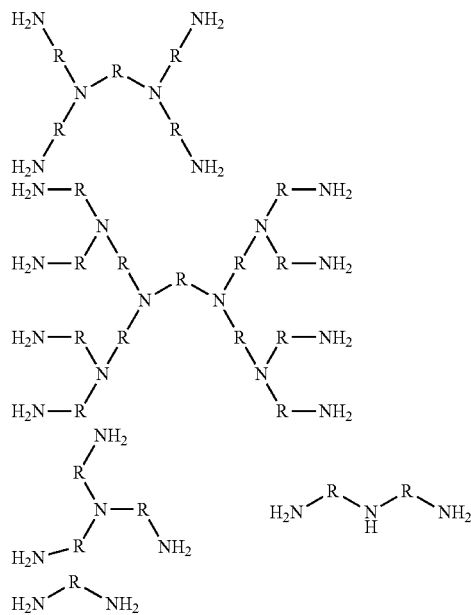

and combinations thereof, wherein R independently represents a branched or unbranched, substituted or unsubstituted alkyl radical.

15. The method of claim 3, wherein the multi-ester is selected from the group consisting of:

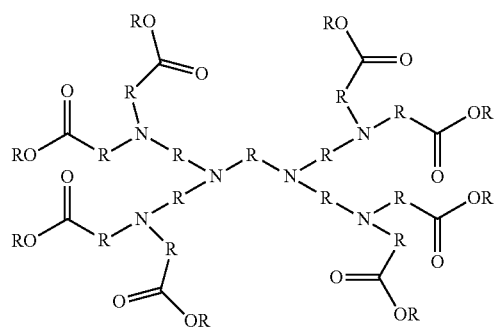

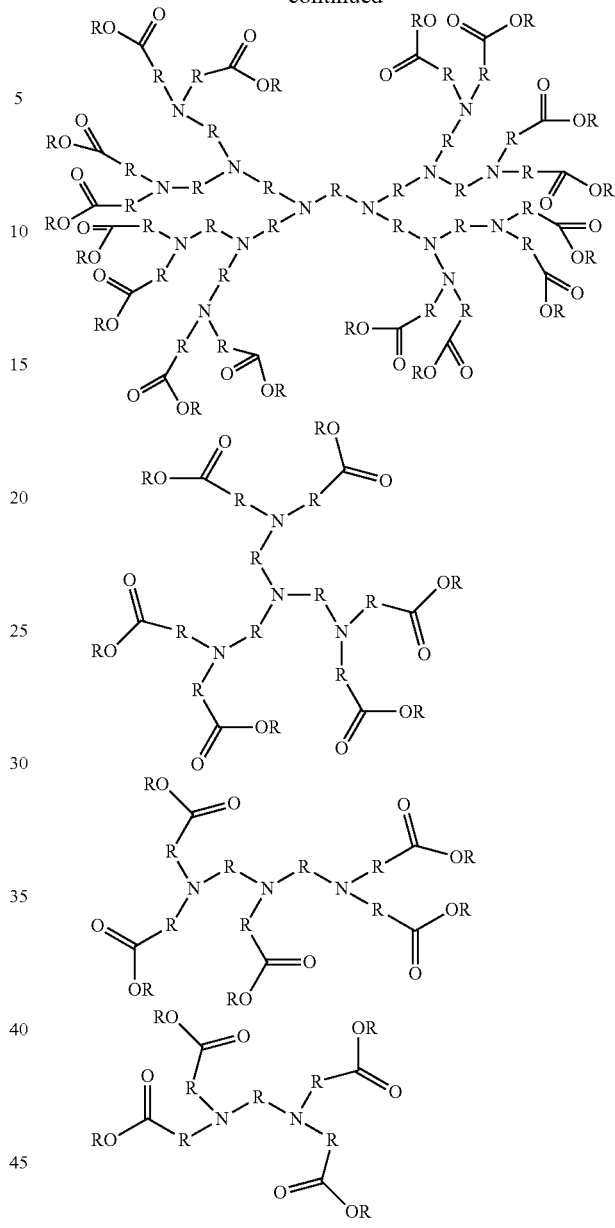

and combinations thereof, wherein R independently represents a branched or unbranched, substituted or unsubstituted alkyl radical.

* * * * *